United States Patent
Mun et al.

(10) Patent No.: US 9,381,260 B2
(45) Date of Patent: Jul. 5, 2016

(54) HYPOXIA INDUCIBLE FACTOR-1 PATHWAY INHIBITORS AND USES AS ANTICANCER AND IMAGING AGENTS

(71) Applicant: EMORY UNIVERSITY, Atlanta, GA (US)

(72) Inventors: Jiyoung Mun, Atlanta, GA (US); Mark M. Goodman, Atlanta, GA (US); Erwin G. Van Meir, Tucker, GA (US)

(73) Assignee: Emory University, Atlanta, GA (US)

( * ) Notice: Subject to any disclaimer, the term of this patent is extended or adjusted under 35 U.S.C. 154(b) by 182 days.

(21) Appl. No.: 13/728,821

(22) Filed: Dec. 27, 2012

(65) Prior Publication Data

US 2013/0164218 A1 Jun. 27, 2013

Related U.S. Application Data

(60) Provisional application No. 61/580,366, filed on Dec. 27, 2011.

(51) Int. Cl.
| | |
|---|---|
| *A61K 51/00* | (2006.01) |
| *A61M 36/14* | (2006.01) |
| *A61K 51/04* | (2006.01) |
| *C07D 311/58* | (2006.01) |
| *A61K 31/352* | (2006.01) |
| *C07D 405/12* | (2006.01) |
| *A61K 31/4433* | (2006.01) |
| *A61K 31/4178* | (2006.01) |
| *C07D 417/12* | (2006.01) |
| *A61K 31/427* | (2006.01) |
| *A61K 45/06* | (2006.01) |

(52) U.S. Cl.
CPC ........... *A61K 51/0455* (2013.01); *A61K 31/352* (2013.01); *A61K 31/4178* (2013.01); *A61K 31/427* (2013.01); *A61K 31/4433* (2013.01); *A61K 45/06* (2013.01); *A61K 51/0421* (2013.01); *A61K 51/0453* (2013.01); *C07D 311/58* (2013.01); *C07D 405/12* (2013.01); *C07D 417/12* (2013.01)

(58) Field of Classification Search
CPC ............ A61K 51/0455; A61K 31/352; A61K 31/4433; A61K 31/4178; A61K 31/427; A61K 45/06; A61K 51/0453; A61K 51/0421; C07D 311/58; C07D 405/12; C07D 417/12
USPC ......................................................... 424/1.89
See application file for complete search history.

(56) References Cited

U.S. PATENT DOCUMENTS

2008/0226622 A1* 9/2008 Van Meir et al. .......... 424/130.1

FOREIGN PATENT DOCUMENTS

| WO | 0220008 A1 | 3/2002 |
|---|---|---|
| WO | 2004087066 A2 | 10/2004 |
| WO | 2007025169 A2 | 3/2007 |
| WO | WO 2007025169 A2 * | 3/2007 |
| WO | 2007136592 A2 | 11/2007 |
| WO | 2008113006 A1 | 9/2008 |
| WO | 2008136756 A1 | 11/2008 |
| WO | 2010006184 A2 | 1/2010 |
| WO | 2010006189 A2 | 1/2010 |
| WO | 2010039977 A2 | 4/2010 |
| WO | 2011133659 A2 | 10/2011 |
| WO | WO 2011133659 A2 * | 10/2011 |

OTHER PUBLICATIONS

Tan et al. Bioorg. Med. Chem. Lett. 21, 2011, 5528-5532.*
Patani et al. Chem. Rev. 1996, 96, 3147-3176.*
Nicolaou et al. JACS 2000, 122, 9954-9967.*
Zhang et al. Curr. Top. Med. Chem., 2007, 7, 1817-1828.*
Lee et al. Semin. Nucl. Med. 2007, 451-361.*
Noan-Minh Chau, et al., (2005), "Identification of Novel Small Molecule Inhibitors of Hypoxia-Inducible Factor-1 that Differentially Block Hypoxia-Inducible Factor-1 Activity and Hypoxia-Inducible Factor-1 α Induction in Response to Hypoxic Stress and Growth Factors.", Cancer Research, 65(11):4918-4928.
Rambabu Gundla, et al., (2008), "Discovery of Novel Small-Molecule Inhibitors of Human Epidermal Growth Factor Receptor-2: Combined Ligand and Target-Based Approach.", Journal of Medicinal Chemistry, 51(12):3367-3377.
Kangae Lee, et al., (2009), "Acriflavine Inhibits HIF-1 Dimerization, Tumor Growth, and Vascularization.", Proceedings of the National Academy of Sciences USA, 106(42):17910-17915.
Suazette Reid Mooring, et al., (2011), "Design and Synthesis of Novel Small-Molecule Inhibitors of the Hypoxia Inducible Factor Pathway.", Journal of Medicinal Chemistry, 54(24): 8471-8489.
Jiyoung Mun, et al., (2012), "Structure-Activity Relationship of 2,2-Dimethyl-2H-Chromene Based Arylsulfonamide Analogs of 3,4-Dimethoxy-N-[(2,2-Dimethyl-2H-Chromen-6-yl)Methyl]-N-Phenylbenzenesulfonamide, a Novel Small Molecule Hypoxia Inducible Factor-1 (HIF-1) Pathway Inhibitor and Anti-Cancer Agent.", Bioorganic & Medicinal Chemistry, 20(14): 4590-4597.
Jiyoung Mun, et al., (2012), "Design and In Vitro Activities of N-Alkyl-N-[(8-R-2,2-dimethyl-2H-Chromen-6-yl)Methyl] Heteroarylsulfonamides, Novel, Small-Molecule Hypoxia Inducible Factor-1 Pathway Inhibitors and Anticancer Agents.", Journal of Medicinal Chemistry, 55(15): 6738-6750.
Takuhito Narita, et al., (2009), "Identification of a Novel Small Molecule HIF-1α Translation Inhibitor.", Clinical Care Research, 15(19): 6128-6136.
K.C. Nicolaou, et al., (2000), "Natural Product-like Combinatorial Libraries Based on Privileged Structures. 2. Construction of a 10000-Membered Benzopyran Library by Directed Split-and-Pool Chemistry Using NanoKans and Optical Encoding.", Journal of the American Chemical Society, 122(41): 9954-9967.

(Continued)

*Primary Examiner* — Michael G Hartley
*Assistant Examiner* — Sean R Donohue
(74) *Attorney, Agent, or Firm* — Emory Patent Group

(57) ABSTRACT

This disclosure relates to Hypoxia Inducible Factor-1 pathway inhibitors and uses as anticancer and imaging agents. In certain embodiments, the disclosure contemplates compounds and pharmaceutical compositions disclosed herein.

9 Claims, 3 Drawing Sheets

(56) References Cited

OTHER PUBLICATIONS

K.C. Nicolaou, et al., (2000), "Natural Product-like Combinatorial Libraries Based on Privileged Structures. 1. General Principles and Solid-Phase Synthesis of Benzopyrans.", Journal of the American Chemical Society, 122(41): 9939-9953.

Eun Jung Park, et al., (2006), "Targeting the PAS-A Domain of HIF-1α for Development of Small Molecule Inhibitors of HIF-1.", Cell Cycle, 5(16): 1847-1853.

George A. Patani, et al., (1996), "Bioisosterism: A Rational Approach in Drug Design.", Chemical Reviews, 96(8):3147-3176.

Soizic Prado, et al., (2007), "Synthesis and Antimycobacterial Evaluation of Benzofurobenzopyran Analogues.", Bioorganic & Medicinal Chemistry, 15(5): 2177-2186.

Chalet Tan, et al., (2005), "Identification of a Novel Small-Molecule Inhibitor of the Hypoxia-Inducible Factor 1 Pathway.", Cancer Research, 65(2): 605-612.

Chalet Tan, et al., (2011), "Sulfonamides as a New Scaffold for Hypoxia Inducible Factor Pathway Inhibitors.", Bioorganic & Medicinal Chemistry Letters, 21(18): 5528-5532.

Shaoman Yin, et al., (2012), "Arylsulfonamide KCN1 Inhibits In Vivo Glioma Growth and Interferes with HIF Signaling by Disrupting HIF-1α Interaction with Cofactors p300/CBP.", Clinical Cancer Research, 18(24): 6623-6633.

Ming-Rong Zhang, et al., (2007), "[18F] Fluoroalkyl Agents: Synthesis, Reactivity and Application for Development of PET Ligands in Molecular Imaging.", Current Topics in Medicinal Chemistry, 7(18): 1817-1828.

* cited by examiner (A) 3,4-Dimethoxy-*N*-[(2,2-dimethyl-2*H*-chromen-6-yl)methyl]-*N*-phenylbenzenesulfonamide (1)

(B) *N*-[(2,2-dimethyl-2*H*-chromen-6-yl)methyl]-*N*-(propan-2-yl)arylsulfonamide (2, 3, 4, 5)

Region 3
(8-*R*-2,2-dimethyl-2*H*-chromen-6-yl)methyl group

Region 1
Heteroarylsulfonyl group

Region 2
*N*-alkyl group (C) *N*-alkyl-*N*-[(8-*R*-2,2-dimethyl-2*H*-chromen-6-yl)methyl]heteroarylsulfonamides

HYPOXIA INDUCIBLE FACTOR-1 PATHWAY INHIBITORS AND USES AS ANTICANCER AND IMAGING AGENTS

CROSS REFERENCE TO RELATED APPLICATIONS

This application claims priority to U.S. Provisional application No. 61/580,366 filed 27 Dec. 2012, hereby incorporated by reference in its entirety.

STATEMENT REGARDING FEDERALLY FUNDED RESEARCH

This invention was made with government support under grants CA128301 and CA116804 awarded by the National Institutes of Health. The Government has certain rights in the invention.

BACKGROUND

The vasculature associated with fast proliferating solid tumors is abnormal, which limits efficient oxygen supply and renders the tumor tissue hypoxic. The presence of hypoxic areas in solid cancers has been correlated with resistance to chemotherapy and radiation treatment. Intratumoral hypoxia induces hypoxia inducible factors (HIFs), transcription factors that activate genes controlling mechanisms such as glycolysis, erythropoiesis, angiogenesis, and cell motility, which can benefit the survival of cancer cells. HIFs can also influence the self-renewal of cancer stem-like cells (CSCs) and be activated in response to growth factors, oncogenes, and inactivation of tumor suppressor genes.

HIFs are heterodimeric protein complexes, composed of HIF-α and HIF-β subunits, which then associate with cofactors such as p300 and CBP to form active transcription factors. The regulation of HIFs largely occurs at the protein level, and is dependent upon the synthesis and stability of the HIF-α subunits. Under normoxia, HIF-α subunits are hydroxylated at proline residues by oxygen-dependent prolyl hydroxylases (PHDs), which mediates recognition by the Von Hippel-Lindau (VHL) E3 ubiquitin ligase complex and rapid degradation by the proteasome. Under hypoxia, HIF-α subunits are stabilized due to the inhibition of proline hydroxylation, and a functional HIF transcriptional complex is assembled, translocates to the nucleus, and transcribes genes that contain DNA sequences called hypoxia response elements (HREs). Elevated levels of HIF-1α have been correlated with poor prognosis of patients with glioblastoma (GBM), breast, pancreatic, colon, and metastatic lung cancers.

Hypoxic tumor and HIF-1 have been evaluated as targets for anticancer therapy using a variety of approaches. While the differential function of HIF-1 and HIF-2 isoforms is still under investigation both are associated with brain cancer stem-like cells, and most studies suggest that one or both isoforms need targeting, depending on tumor and cancer type. Therefore, tumor cells overexpressing HIF represent an important target for antitumor therapy.

A number of existing chemotherapeutics can alter HIF activity as a result of their pleiotropic effects, including 2ME2, 17-DMAG, 17-AAG, camptothecin, PX-478, and YC-1. Most of the agents studied affect HIF indirectly via the inhibition of microtubule polymerization, Hsp90, topoisomerase I, thioredoxin 1, or other unknown mechanisms. A search for more specific inhibitors used a screen targeting the interaction of HIF with the key transcriptional coactivator p300. A recent study suggests that acriflavine, an antitrypanocidal, antibacterial, and antiviral agent interferes with HIF-1α and -1β dimerization and possibly other signaling pathways such as NF-κB. It is also desirable to develop several agents that can interfere with HIF transcription in different ways so that we are prepared for the development of tumor resistance against single targeted sites.

SUMMARY

This disclosure relates to Hypoxia Inducible Factor-1 pathway inhibitors and uses as anticancer and imaging agents. In certain embodiments, the disclosure contemplates compounds and pharmaceutical compositions. In certain embodiment, the disclosure contemplates compounds disclosed herein as prodrugs, optionally substituted with one or more substituents, derivatives, or salts thereof.

In certain embodiments, the disclosure relates to compounds of the formula

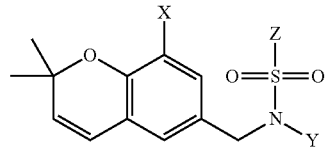

or salts thereof, wherein

X is H, hydrogen, hydroxy, methoxy, ethoxy, 2-fluoroethoxy, 3-fluoropropanoxy, 2-(morpholin-4-yl)ethoxy, and 2-(piperazin-1-yl)ethoxy, wherein X is optionally substituted with one or more, the same or different $R^1$;

Y is alkyl isopropyl, cyclopropyl, tert-butyl, cyclobutyl, cyclopentyl, cyclohexyl, isobutyl, cyclopropanemethyl, 1-propynyl, 2-fluoroethyl, 3-fluoropropyl and 1,3-difluoro-2-propyl, wherein Y is optionally substituted with one or more, the same or different $R^1$;

Z is 2-pyridinyl, 3-pyridinyl, 4-pyridinyl, 4-chloro-3-pyridinyl, 2-chloro-3-pyridinyl, 4-cyano-3,5-dimethyl-2-pyridinyl, 4-trifluoromethyl-2-pyridinyl, 4-cyano-2-pyridinyl, 2-thiophenyl, 2-1-methylimidazolyl, 2-benzothiazolyl, 2-thiazolyl, 2-quinolinyl, 2-pyrimidyl, 2-pyrazinyl, 2-imidazolyl, 2,5-methyl-1,3,4-thiadiazolyl, 5-1-methyltetrazolyl, 2,5-methoxybenzothiazolyl, 2-benzimidazolyl, 2-5-methylbenzimidazolyl, 6-purinyl, 2-benzoxazolyl, 2-4-methylthiazolyl, 2-4-methylpyrimidinyl, and 4-cyano-2-pyridinyl wherein Y is optionally substituted with one or more, the same or different $R^1$;

$R^1$ is alkyl, halogen, nitro, cyano, hydroxy, amino, mercapto, formyl, carboxy, alkanoyl, carbamoyl, alkoxy, alkylthio, alkylamino, (alkyl)$_2$-amino, alkylsulfinyl, alkylsulfonyl, arylsulfonyl, carbocyclyl, aryl, or heterocyclyl, wherein $R^1$ is optionally substituted with one or more, the same or different, $R^2$; and $R^2$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiment, X is OH optionally substituted with one or more, the same or different $R^1$.

In certain embodiments, the compound comprises a tracer for PET imaging such as carbon 11 or fluorine 18.

In certain embodiments, the disclosure contemplates pharmaceutical compositions comprising compounds disclosed herein or a pharmaceutically acceptable salt and a pharmaceutically acceptable excipient.

In certain embodiments, the disclosure contemplates methods of treating or preventing cancer comprising administering an effective amount of a pharmaceutical composition disclosed herein. In some embodiments, the cancer is selected from glioblastoma (GBM), breast, pancreatic, colon, metastatic lung cancers, bladder cancer, lung cancer, breast cancer, melanoma, colon and rectal cancer, non-hodgkin lymphoma, endometrial cancer, pancreatic cancer, kidney cancer, prostate cancer, leukemia, thyroid cancer, and brain cancer.

In some embodiments, the methods contemplate that the compositions are administered in combination with a second anti-cancer agent such as is temozolamide, bevacizumab, procarbazine, lomustine, vincristine, gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vinblastine, vindesine, vinorelbine, taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, combretastatin, thalidomide, and/or lenalidomide or combinations thereof.

In certain embodiments, the disclosure contemplates methods of imaging a tumor comprising administering a compound disclosed herein with a tracer to a subject and viewing the compound by PET.

In certain embodiments, the disclosure contemplates methods of preparing compounds disclosed herein by mixing starting materials under conditions such that the compounds are formed.

DETAILED DISCUSSION

Figure 1:
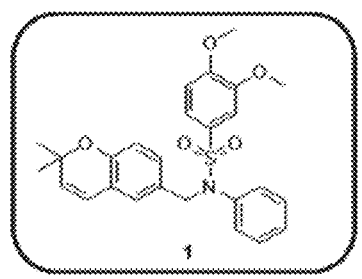
FIG. 1 illustrates embodiments of N-alkyl-N-[(8-R-2,2-dimethyl-2H-chromen-6-yl)methyl]heteroarylsulfonamides.
Figure 1:
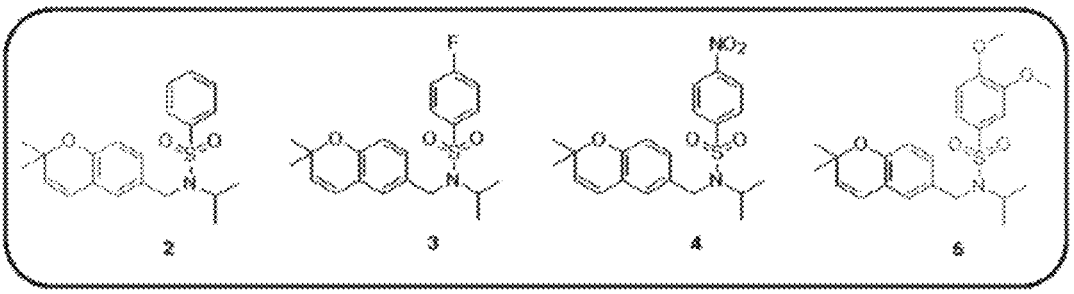
Figure 1:
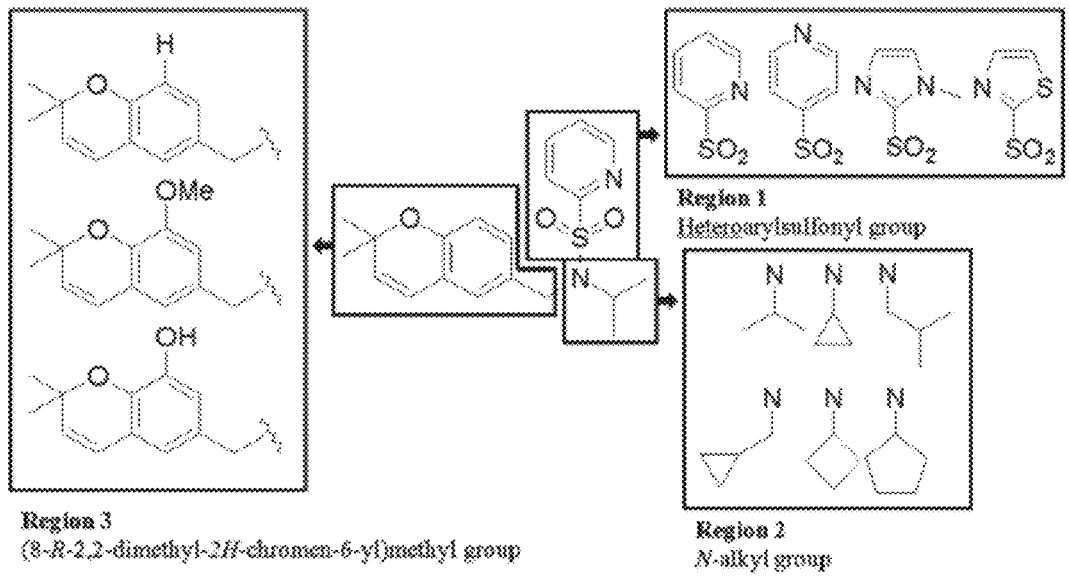

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, "alkyl" means a noncyclic straight chain or branched, unsaturated or saturated hydrocarbon such as those containing from 1 to 22 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 8 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or "heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH3).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, and t-butoxy.

"Alkylamino" refers an alkyl group as defined above attached through an amino bridge. An example of an alkylamino is methylamino, (i.e., —NH—CH3).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfinyl" refers to an alkyl as defined above attached through a sulfinyl bridge (i.e. —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In typical embodiments, the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, rodent, monkey or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "derivative" refers to a structurally similar compound that retains sufficient functional attributes of the identified analogue. The derivative may be structurally similar because it is lacking one or more atoms, substituted with one or more substituents, a salt, in different hydration/oxidation states, e.g., substituting a single or double bond, substituting a hydroxy group for a ketone, or because one or more atoms within the molecule are switched, such as, but not limited to, replacing an oxygen atom with a sulfur or nitrogen atom or replacing an amino group with a hydroxyl group or vice versa. Replacing a carbon with nitrogen in an aromatic ring is a contemplated derivative. The derivative may be a prodrug. Derivatives may be prepared by any variety of synthetic methods or appropriate adaptations presented in the chemical literature or as in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

N-alkyl-N-[(8-R-2,2-dimethyl-2H-chromen-6-yl) methyl]heteroarylsulfonamides

Ongoing investigations have identified the CH1 domain of p300/CBP as the putative target of 1, and its binding is expected to disrupt the formation of the transcriptional complex among HIF-1α, HIF-1β, and p300/CBP under hypoxia. 1 showed anticancer activity in vivo in brain, eye, and pancreatic cancer mouse models; however, it necessitated delivery in a formulation (Cremophor:ethanol=1:1) due to poor aqueous solubility (0.009 µM). To develop analogs of 1 with improved aqueous solubility, we previously investigated structure-activity relationships of 15 lipophilic analogs and selected N-[(2,2-dimethyl-2H-chromene-6-yl)methyl]-N-(propan-2-yl)arylsulfonamides as the molecular motifs for further modifications described in the current study. See Mun et al. Bioorganic & Medicinal Chemistry 20 (2012) 4590-4597, hereby incorporated by reference in its entirety.

N-alkyl-N-[(8-R-2,2-dimethyl-2H-chromen-6-yl)methyl] heteroarylsulfonamides (abbreviated hereafter as "heteroarylsulfonamides") were designed to possess molecular weights and estimated log P and log $S_w$ values optimal for lead compounds in drug discovery. Heteroarylsulfonamides were synthesized, and their inhibition potency against the transcriptional activity of HIF-1, effect on HIF-1α synthesis and stability, physicochemical properties, metabolic stabilities, and cytotoxicities in human glioma and fibroblast cells were measured.

As in FIG. 1, compound 1 is a potent HIF-1 pathway inhibitor with a cell-based high-throughput assay. 1 contains a 2,2-dimethyl-2H-chromene ring found in many natural products. For example, 2,2-dimethyl-2H-chromene-based molecules isolated from *Blepharispermum subsessile* and the leaves of *Piper aduncum* L. have antifungal, antibacterial, and trypanocidal activities. The chromenes extracted from the leaves of *Melicope lunu-ankenda* have antipyretic, analgesic, anti-inflammatory, and antioxidant activities. Further structure-activity relationship (SAR) studies on 1 showed that N-[(2,2-dimethyl-2H-chromen-6-yl)methyl]-N-(propan-2-yl)arylsulfonamides possess strong HIF-1 pathway inhibition and are amenable for further chemical optimization.

A series of 2,2-dimethyl-2H-chromene-based heteroarylsulfonamides were designed with the purpose of decreasing lipophilicity and increasing aqueous solubility. The N-[(2,2-dimethyl-2H-chromen-6-yl)methyl]-N-(propan-2-yl)arylsulfonamides were modified by substituting the arylsulfonyl group in region 1 with heteroarylsulfonyl groups such as pyridine-2-sulfonyl, pyridine-4-sulfonyl, 1-methyl-1H-imidazole-2-sulfonyl, and thiazole-2-sulfonyl groups; by replacing the propan-2-yl group in region 2 with short alkyl groups that mainly consist of small cyclic alkyl groups; and by derivatizing the chromene moiety at the C-8 position in region 3.

Heteroarylsulfonamides were designed to possess optimal log P and log $S_w$ values by in silico calculations and subsequently synthesized. All 12 heteroarylsulfonamides show inhibition of HIF-1 transcription in a reporter assay at low micromolar concentrations, and the mechanism of action appeared independent of alteration in HIF-1α protein expression. Ongoing studies suggest that the mechanism of action of 1 involves the disruption of the interaction between HIF-1α and its cofactors p300/CBP by antagonizing the CH1 domain of p300.

Eight heteroarylsulfonamides showed lower log $P_{7.4}$ values ranging from 1.2 to 3.1 versus 3.7 for 1. Increased aqueous solubilities were achieved for compounds 6a, 6d, and 6g, which were 100, 20, and 9000 times more soluble than 1, respectively. The stabilities of 6a, 6d, 6g, and 6l in mouse plasma were similar to that of the parent compound 1; however, they exhibited longer half-lives in homogenized mouse liver, ranging from 13 to 20 h, compared with 11 h for 1, which suggests that they will likely be more resistant to in vivo hepatic metabolism than 1.

Six-membered heteroaryl groups in region 1, a propan-2-amine in region 2, and a (6-hydroxy-2,2-dimethyl-2H-chromen-6-yl)methyl group in region 3 increased the aqueous solubility and HIF-1 inhibition and decrease lipophilicity. 1-Cyclopropylmethanamine and cyclobutanamine in region 2 showed better HIF-1 inhibition than propan-2-amine; however, lipophilicity, aqueous solubility, and metabolic stability made the latter group the superior choice.

Cancer

In a typical embodiment, the disclosure relates to a method treating or preventing cancer comprising administering to a patient a compound disclosed herein disclosed herein. In some embodiments, the disclosure relates to a compound disclosed herein, or a pharmaceutically acceptable salt thereof for uses in treating cancer.

In some embodiments, the disclosure relates to a compound disclosed herein, or a pharmaceutically acceptable salt thereof, as defined herein for use in the treatment of cancer of the breast, colorectum, lung (including small cell lung cancer, non-small cell lung cancer and bronchioalveolar cancer) and prostate.

In some embodiments, the disclosure relates to a compound disclosed herein, or a pharmaceutically acceptable salt thereof, as defined herein for use in the treatment of cancer of the bile duct, bone, bladder, head and neck, kidney, liver, gastrointestinal tissue, oesophagus, ovary, endometrium, pancreas, skin, testes, thyroid, uterus, cervix and vulva, and of leukaemias (including ALL and CML), multiple myeloma and lymphomas.

In some embodiments, the disclosure relates to a compound disclosed herein, or a pharmaceutically acceptable salt thereof, as defined herein for use in the treatment of lung cancer, prostate cancer, melanoma, ovarian cancer, breast cancer, endometrial cancer, kidney cancer, gastric cancer, sarcomas, head and neck cancers, tumors of the central nervous system and their metastases, and also for the treatment of glioblastomas.

In some embodiments, compounds disclosed herein could be used in the clinic either as a single agent by itself or in combination with other clinically relevant agents. This compound could also prevent the potential cancer resistance mechanisms that may arise due to mutations in a set of genes.

The anti-cancer treatment defined herein may be applied as a sole therapy or may involve, in addition to the compound of the disclosure, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon;

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab), farnesyl transferase inhibitors, tyrosine kinase inhibitors and serine/threonine kinase inhibitors, for example inhibitors of the epidermal growth factor family (for example EGFR family tyrosine kinase inhibitors such as: N-(3-chloro-4-fluorophenyl)-7-methoxy-6-(3-morpholinopropoxy) quinazolin-4-amine (gefitinib), N-(3-ethynylphenyl)-6,7-bis (2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet-derived growth factor family and for example inhibitors of the hepatocyte growth factor family, for example inhibitors or phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (Abl) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin αvβ3 function and angiostatin);

(vi) vascular damaging agents such as Combretastatin A4;

(vii) antisense therapies, for example those which are directed to the targets listed above, such as an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies, and approaches using the immunomodulatory drugs thalidomide and lenalidomide [Revlimid®].

Such conjoint treatment may be achieved by way of the simultaneous, sequential or separate dosing of the individual components of the treatment. Such combination products employ the compounds of this disclosure, or pharmaceutically acceptable salts thereof, within the dosage range described hereinbefore and the other pharmaceutically-active agent within its approved dosage range.

Positron Emission Tomography

The tracers for positron emission tomography (PET) have been used in the clinical phase of drug developments. Pharmacokinetic and pharmacodynamic properties of the drugs can be obtained noninvasively in PET, so more detailed information can be obtained from PET compared to invasive pathologic methods. The PET tracers can also be used for patient selections in target-specific therapies by measuring target protein concentrations or binding potentials of the tracers. The utilization of the drug itself as the tracer for PET have several unique advantages: first, the time dependent concentration of a drug at a region of interest can be measured, which enables the rational design of dose regimen of the drug.; second, the plasma metabolism of the drug can be measured with high sensitivity; third, the drug uptake into normal tissues can be measured, which enables the prediction of toxicity. Here, tracers were designed for PET from compounds disclosed herein to utilize them to measure the pharmacokinetics of the drugs and the pharmacodynamics of the similar drugs that target HIF-1 pathways.

In certain embodiments, the disclosure relates to compounds of the formula

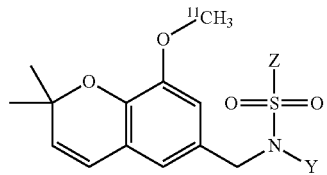

or salts thereof, wherein

Y is alkyl isopropyl, cyclopropyl, tert-butyl, cyclobutyl, cyclopentyl, cyclohexyl, isobutyl, cyclopropanemethyl, 1-propynyl, 2-fluoroethyl, 3-fluoropropyl and 1,3-difluoro-2-propyl, wherein Y is optionally substituted with one or more, the same or different $R^1$;

Z is 2-pyridinyl, 3-pyridinyl, 4-pyridinyl, 4-chloro-3-pyridinyl, 2-chloro-3-pyridinyl, 4-cyano-3,5-dimethyl-2-pyridinyl, 4-trifluoromethyl-2-pyridinyl, 4-cyano-2-pyridinyl, 2-thiophenyl, 2-1-methylimidazolyl, 2-benzothiazolyl, 2-thiazolyl, 2-quinolinyl, 2-pyrimidyl, 2-pyrazinyl, 2-imidazolyl, 2,5-methyl-1,3,4-thiadiazolyl, 5-1-methyltetrazolyl, 2,5-methoxybenzothiazolyl, 2-benzimidazolyl, 2-5-methylbenzimidazolyl, 6-purinyl, 2-benzoxazolyl, 2-4-methylthiazolyl, 2-4-methylpyrimidinyl, and 4-cyano-2-pyridinyl wherein Y is optionally substituted with one or more, the same or different $R^1$;

$R^1$ is alkyl, halogen, nitro, cyano, hydroxy, amino, mercapto, formyl, carboxy, alkanoyl, carbamoyl, alkoxy, alkylthio, alkylamino, (alkyl)$_2$-amino, alkylsulfinyl, alkylsulfonyl, arylsulfonyl, carbocyclyl, aryl, or heterocyclyl, wherein $R^1$ is optionally substituted with one or more, the same or different, $R^2$; and $R^2$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In one embodiment, the disclosure contemplates compounds provided in the scheme below.

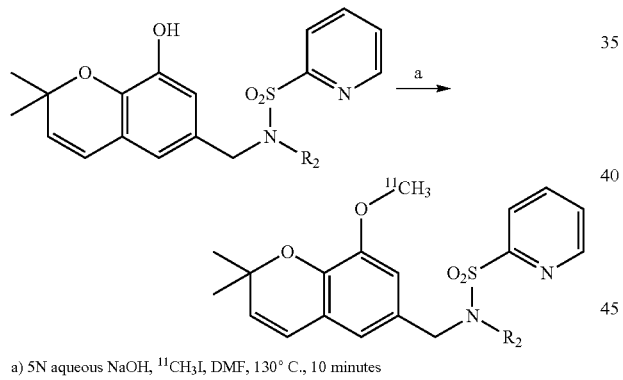

a) 5N aqueous NaOH, $^{11}CH_3I$, DMF, 130° C., 10 minutes

In certain embodiments, the disclosure relates to compounds of the formula

In certain embodiments, the disclosure relates to compounds of the formula

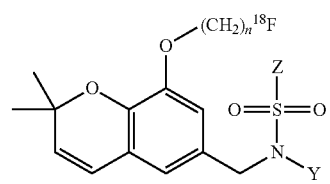

or salts thereof, wherein
n is 1-8, or 2, or 3;
Y is alkyl isopropyl, cyclopropyl, tert-butyl, cyclobutyl, cyclopentyl, cyclohexyl, isobutyl, cyclopropanemethyl, 1-propynyl, 2-fluoroethyl, 3-fluoropropyl and 1,3-difluoro-2-propyl, wherein Y is optionally substituted with one or more, the same or different $R^1$;

Z is 2-pyridinyl, 3-pyridinyl, 4-pyridinyl, 4-chloro-3-pyridinyl, 2-chloro-3-pyridinyl, 4-cyano-3,5-dimethyl-2-pyridinyl, 4-trifluoromethyl-2-pyridinyl, 4-cyano-2-pyridinyl, 2-thiophenyl, 2-1-methylimidazolyl, 2-benzothiazolyl, 2-thiazolyl, 2-quinolinyl, 2-pyrimidyl, 2-pyrazinyl, 2-imidazolyl, 2,5-methyl-1,3,4-thiadiazolyl, 5-1-methyltetrazolyl, 2,5-methoxybenzothiazolyl, 2-benzimidazolyl, 2-5-methylbenzimidazolyl, 6-purinyl, 2-benzoxazolyl, 2-4-methylthiazolyl, 2-4-methylpyrimidinyl, and 4-cyano-2-pyridinyl wherein Y is optionally substituted with one or more, the same or different $R^1$;

$R^1$ is alkyl, halogen, nitro, cyano, hydroxy, amino, mercapto, formyl, carboxy, alkanoyl, carbamoyl, alkoxy, alkylthio, alkylamino, (alkyl)$_2$-amino, alkylsulfinyl, alkylsulfonyl, arylsulfonyl, carbocyclyl, aryl, or heterocyclyl, wherein $R^1$ is optionally substituted with one or more, the same or different, $R^2$; and $R^2$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to compounds of the formula

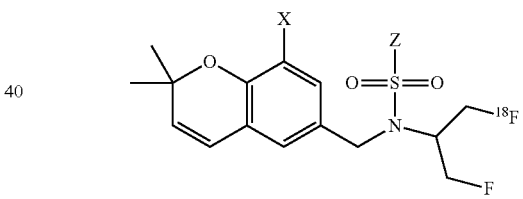

or salts thereof, wherein
X is H, hydrogen, hydroxy, methoxy, ethoxy, 2-fluoroethoxy, 3-fluoropropanoxy, 2-(morpholin-4-yl)ethoxy, and 2-(piperazin-1-yl)ethoxy, wherein X is optionally substituted with one or more, the same or different $R^1$;

Z is 2-pyridinyl, 3-pyridinyl, 4-pyridinyl, 4-chloro-3-pyridinyl, 2-chloro-3-pyridinyl, 4-cyano-3,5-dimethyl-2-pyridinyl, 4-trifluoromethyl-2-pyridinyl, 4-cyano-2-pyridinyl, 2-thiophenyl, 2-1-methylimidazolyl, 2-benzothiazolyl, 2-thiazolyl, 2-quinolinyl, 2-pyrimidyl, 2-pyrazinyl, 2-imidazolyl, 2,5-methyl-1,3,4-thiadiazolyl, 5-1-methyltetrazolyl, 2,5-methoxybenzothiazolyl, 2-benzimidazolyl, 2-5-methylbenzimidazolyl, 6-purinyl, 2-benzoxazolyl, 2-4-methylthiazolyl, 2-4-methylpyrimidinyl, and 4-cyano-2-pyridinyl wherein Y is optionally substituted with one or more, the same or different $R^1$;

$R^1$ is alkyl, halogen, nitro, cyano, hydroxy, amino, mercapto, formyl, carboxy, alkanoyl, carbamoyl, alkoxy, alkylthio, alkylamino, (alkyl)$_2$-amino, alkylsulfinyl, alkylsulfonyl, arylsulfonyl, carbocyclyl, aryl, or heterocyclyl, wherein $R^1$ is optionally substituted with one or more, the same or different, $R^2$; and R² is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to compounds of the formula

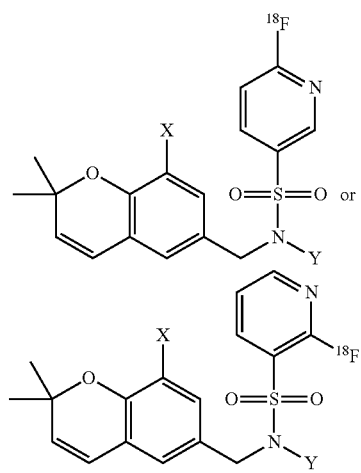

or salts thereof, wherein

X is H, hydrogen, hydroxy, methoxy, ethoxy, 2-fluoroethoxy, 3-fluoropropanoxy, 2-(morpholin-4-yl)ethoxy, and 2-(piperazin-1-yl)ethoxy, wherein X is optionally substituted with one or more, the same or different R¹;

Y is alkyl isopropyl, cyclopropyl, tert-butyl, cyclobutyl, cyclopentyl, cyclohexyl, isobutyl, cyclopropanemethyl, 1-propynyl, 2-fluoroethyl, 3-fluoropropyl and 1,3-difluoro-2-propyl, wherein Y is optionally substituted with one or more, the same or different R¹;

R¹ is alkyl, halogen, nitro, cyano, hydroxy, amino, mercapto, formyl, carboxy, alkanoyl, carbamoyl, alkoxy, alkylthio, alkylamino, (alkyl)₂-amino, alkylsulfinyl, alkylsulfonyl, arylsulfonyl, carbocyclyl, aryl, or heterocyclyl, wherein R¹ is optionally substituted with one or more, the same or different, R²; and R² is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure contemplates compounds provided below.

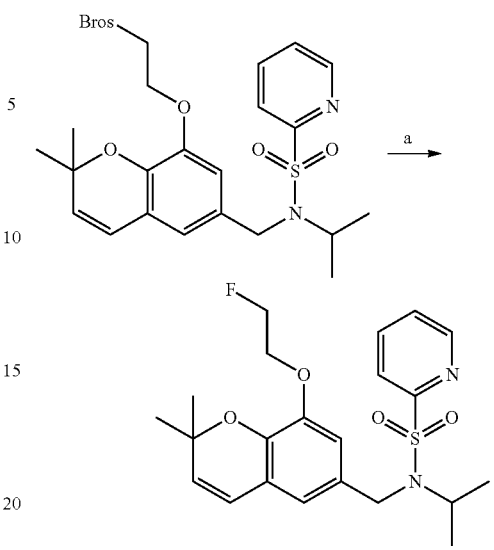

Bros = 4-bromobenzenesulfonyl
a. K¹⁸F, K₂CO₃, K₂,₂,₂, CH₃CN, 110° C., 30 minutes Formulations Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound of the disclosure contains a hydrogen-donating heteroatom (e.g., NH), the disclosure also covers salts and/or isomers formed by the transfer of the hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It is well within the ordinary skill of the art to make an ester prodrug, e.g., acetyl ester of a free hydroxyl group. It is well known that ester prodrugs are readily degraded in the body to release the corresponding alcohol. See e.g., Imai, Drug Metab Pharmacokinet (2006) 21(3):173-85, entitled "Human carboxylesterase isozymes: catalytic properties and rational drug design."

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g., about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly(acrylic acid); poly(hydroxyalkylmethacrylates) (for example poly (hydroxyethyl methacrylate)); carboxypolymethylene (for example Carbopol™); carbomer; polyvinyl pyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethyl cellulose (HMC), hydroxyethylcellulose (HEC), hydroxypropylcellulose (HPC), methylcellulose (MC), ethylcellulose (EC), carboxyethylcellulose (CEC), ethylhydroxy ethylcellulose (EHEC), carboxymethylhydroxyethylcellulose (CMHEC), hydroxypropylmethylcellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Proteins can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (PEGylation) to increase the in vivo half-life of circulating therapeutic proteins and decrease the chance of an immune response.

EXAMPLES

Design of N-Alkyl-N-[(8-R-2,2-dimethyl-2H-chromen-6-yl)methyl]heteroarylsulfonamides The heteroarylsulfonamides were designed on the basis of N-[(2,2-dimethyl-2H-chromen-6-yl)methyl]-N-(propan-2-yl)arylsulfonamides (2-5, FIG. 1). Heteroarylsulfonyl groups were used in region 1 instead of arylsulfonyl groups to increase aqueous solubility. Small alkyl groups were used in region 2, to retain biological activity without abruptly increasing lipophilicity. The 2,2-dimethyl-2H-chromene structure in region 3 was diversified at the C-8 position by adding a hydroxyl or methoxy group due to synthetic feasibility. A hydroxyl group is advantageous in that it can be an anchor for functional groups to further increase the diversity and structural flexibility of the compounds. Twelve heteroarylsulfonamides (6a-6l) were selected for synthesis (Table 1) Their molecular weights range from 371 to 403 g/mol, log P values from 3.4 to 4.2, and log $S_w$ values from −4.2 to −3.2, which are optimal for lead compounds in drug discovery.

Synthesis of N-Alkyl-N-[(8-R-2,2-dimethyl-2H-chromen-6-yl)methyl]heteroarylsulfonamides The chromene ring of 8-R-2,2-dimethyl-2H-chromene-6-carbaldehydes (7a, 7b) was formed by Claisen cyclization of the propargyl ether, 3-R-4-[(2-methylbut-3-yn-2-yl)oxy]benzaldehyde. The N-[(8-R-2,2-dimethyl-2H-chromen-6-yl)methyl]alkylamines (8a-8g) were synthesized from 7a and 7b by acid-catalyzed imine formation and then subsequent reduction with diisobutylaluminum hydride (DIBAL).

The final N-alkyl-N-[(8-R-2,2-dimethyl-2H-chromen-6-yl)methyl]heteroarylsulfonamides (6a-6g, 6i-6k) were synthesized from 8a-8g and heteroarylsulfonyl chlorides. Several synthetic methods have been developed for the preparation of heteroarylsulfonyl chlorides, which are unstable molecules. These include low-temperature oxidative chlorination of thioheterocycles with chlorine gas, chlorination of heteroaromatic methyl sulfides with sulfuryl chloride, oxidation of heteroaromatic thiols in a cosolvent of methylene chloride and 1 N aqueous hydrochloric acid containing 25 wt % calcium chloride with aqueous sodium hypochlorite, and oxidation of heteroaromatic thiols in concentrated sulfuric acid with aqueous sodium hypochlorite. Heteroarylsulfonyl chlorides were synthesized by the last method due to facile reaction conditions. Slow addition of aqueous sodium hypochlorite solution to the reaction mixture was crucial for the high yield of the reaction, since low temperature has to be maintained during the highly exothermic reaction to prevent decomposition of the resulting heteroarylsulfonyl chlorides. The final heteroarylsulfonamides were formed in the presence of triethylamine at 40° C. (refluxing methylene chloride) in the case of pyridine-2-sulfonyl chloride, but in N,N-diisopropylethylamine (NIEA, Hünig's base) at 0° C. for pyridine-4-sulfonyl chloride, 1-methyl-1H-imidazol-2-sulfonyl chloride, and 1,3-thiazol-2-sulfonyl chloride, since the latter heteroarylsulfonyl chlorides decomposed above 0° C. For the reactions at 0° C., the reaction mixture was gradually concentrated by argon gas to accelerate the reactions (Scheme 1).

Scheme 1. Synthesis of N-Alkyl-N-[(8-R-2,2-dimethyl-2H-chromen-6-yl)methyl]heteroarylsulfonamides

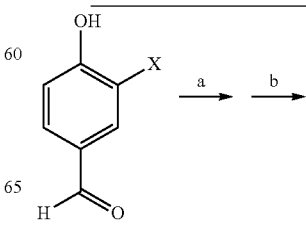

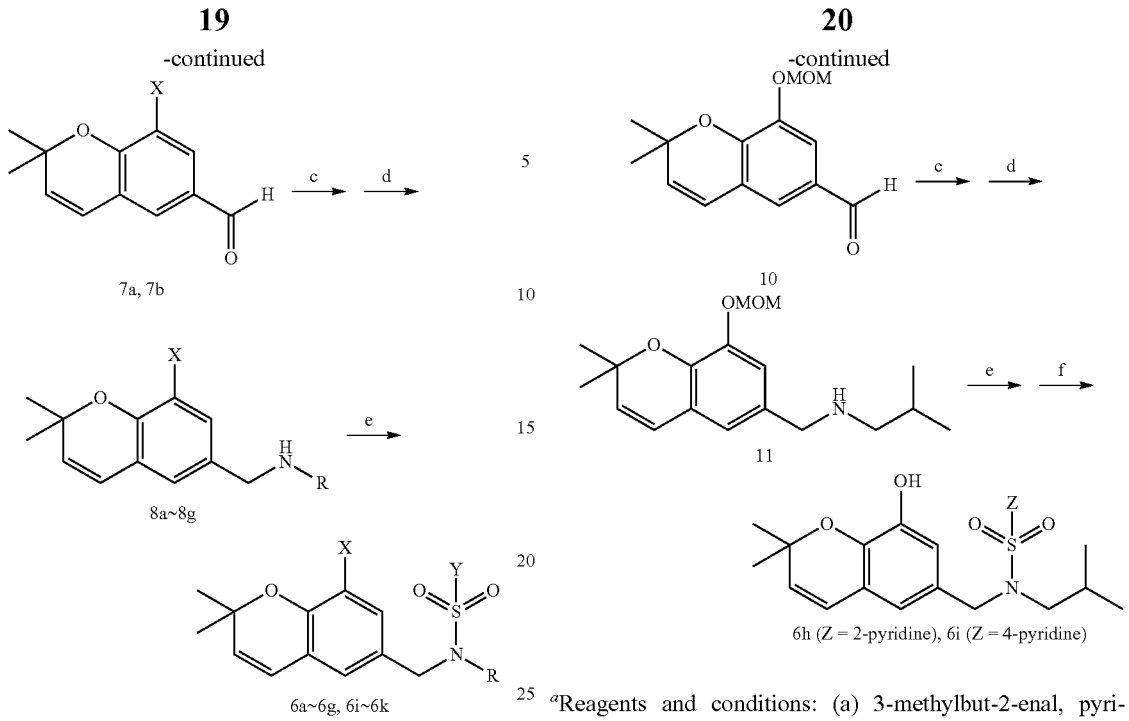

Reagents and conditions: (a) 3-chloro-3-methyl-1-butyne, 4 N aq NaOH, DMF, 60° C., overnight; (b) N-methylpyrrolidone (NMP), reflux, overnight (15% in two steps); (c) alkylamine (propan-2-amine, cyclopropanamine, 2-methylpropan-1-amine, 1-cyclopropylmethanamine, cyclobuthanamine, cyclopenthanamine), p-toluenesulfonic acid monohydrate, methylene chloride, reflux, overnight; (d) diisobutylaluminum hydride (DIBAL), toluene, overnight (39-89% in two steps); (e) heteroarylsulfonyl chloride, triethylamine, methylene chloride, reflux, overnight, or heteroarylsulfonyl chloride, N,N-diisopropylethylamine, methylene chloride, 0° C. to room temperature, overnight (17-77%).

Insertion of a hydroxyl group at the C-8 position of the 2,2-dimethyl-2H-chromene ring was accomplished by chromenylation of 3,4-dihydroxybenzaldehyde with 3-methylbut-2-enal, for which the yield was low and not optimized. The hydroxyl group at the C-8 position of the chromene ring was protected with methyl chloromethyl ether (MOMCl) to form a methoxymethyl ether, which was deprotected by 6 N aqueous HCl mixed with 1 equiv of tetrahydrofuran (THF) at the end of the synthesis (Scheme 2).

Scheme 2. Synthesis of N-[(8-Hydroxy-2,2-dimethyl-2H-chromen-6-yl)methyl]-N-(2-methylpropan-1-yl)pyridine-2-sulfonamide (6h) and N-[(8-Hydroxy-2,2-dimethyl-2H-chromen-6-yl)methyl]-N-(2-methylpropan-1-yl)pyridine-4-sulfonamide (6i)[a]

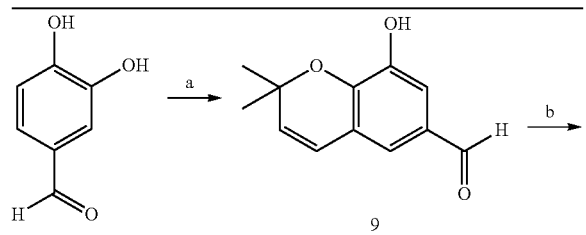

[a]Reagents and conditions: (a) 3-methylbut-2-enal, pyridinium trifluoromethanesulfonate, pyridine, reflux, 2 days (2.4%); (b) chloromethyl methyl ether, N,N-diisopropylethylamine, tetrahydrofuran, reflux, overnight (38%); (c) 2-methylpropan-1-amine, p-toluenesulfonic acid monohydrate, methylene chloride, reflux, overnight; (d) 1 M diisobutylaluminium hydride (DIBAL) in toluene, methylene chloride/toluene (1/2 (v/v)), overnight (13% in two steps); (e) pyridine-2-sulfonyl chloride, triethylamine, methylene chloride, reflux, overnight (for 6h), or pyridine-4-sulfonyl chloride, N,N-diisopropylethylamine, methylene chloride, 0° C. to room temperature, overnight (for 6I); (f) 6 N aqueous HCl, tetrahydrofuran, 3 h (48-49% in two steps).

Synthesis 2,2-Dimethyl-2H-chromene-6-carbaldehyde or 8-Methoxy-2,2-dimethyl-2H-chromene-6-carbaldehyde (7a, 7b)

An aqueous sodium hydroxide solution (4 N, 5 mL) was added to a solution of 4-hydroxybenzaldehyde (2.38 g, 19.5 mmol) and 3-chloro-3-methyl-1-butyne (1 g, 9.75 mmol) in 8 mL of dimethylformamide (DMF), to form a binary solution. The reaction mixture was stirred vigorously at 60° C. overnight. After cooling, 20 mL of water was added to the reaction mixture, which was extracted with diethyl ether (30 mL×3). The combined organic phase was washed with 40 mL of 1 N aqueous sodium hydroxide and then brine, dried with anhydrous magnesium sulfate, and concentrated in vacuo. Formation of crude 4-[(2-methylbut-3-yn-2-yl)oxy]benzaldehyde was confirmed by TLC with ethyl acetate/hexane (1/8) and NMR. $^1$H NMR (CDCl$_3$): δ 1.73 (s, 6H), 2.67 (s, 1H), 7.34 (d, J=8.8 Hz, 1H), 7.83 (d, J=8.8 Hz, 1H), 9.91 (s, 1H).

Crude 4-[(2-methylbut-3-yn-2-yl)oxy]benzaldehyde was dissolved in 10 mL of N-methylpyrrolidone (NMP, bp=202-204° C.) and refluxed overnight. After cooling to room temperature, 80 mL of water was added to the solution, which was extracted with diethyl ether (100 mL×3). The combined organic phase was washed with brine, dried with anhydrous magnesium sulfate, and concentrated in vacuo. 7a was purified by silica gel chromatography with ethyl acetate/hexane (1/8) as a viscous yellowish liquid (565 mg, 15% yield). $^1$H NMR (CDCl$_3$): δ 1.46 (s, 6H), 5.68 (d, J=9.9 Hz, 1H), 6.36 (d, J=9.9 Hz, 1H), 6.85 (d, J=8.05 Hz, 1H), 7.50 (d, J=2.37 Hz, 1H), 7.63 (dd, J=8.52, 1.89 Hz, 1H), 9.83 (s, 1H). HRMS (m/z): M$^+$ calcd 189.09101, found 189.09071.

7b was synthesized by the same method as 7a. Vanillin (3 g, 20 mmol) and 3-chloro-3-methyl-1-butyne (1 g, 10 mmol) were used as starting materials. 7b was purified by silica gel chromatography with ethyl acetate/hexane (1/6) as a white solid (204 mg, 5% in two steps)

3-Methoxy-4-[(2-methylbut-3-yn-2-yl)oxy]benzaldehyde $^1$H NMR (CDCl$_3$): δ 1.75 (s, 6H), 2.63 (s, 1H), 3.90 (s, 3H), 7.43-7.40 (m, 2H), 7.64 (d, J=8.79 Hz, 1H).

8-Methoxy-2,2-dimethyl-2H-chromene-6-carbaldehyde (7b)

$^1$H NMR (CDCl$_3$): δ 1.51 (s, 6H), 3.93 (s, 3H), 5.70 (d, J=9.78 Hz, 1H), 6.37 (d, J=9.78 Hz, 1H), 7.17 (d, J=1.96 Hz, 1H), 7.32 (d, J=1.96 Hz, 1H), 9.81 (s, 1H). HRMS (m/z): M$^+$ calcd 219.10157, found 219.10124.

N-[(2,2-Dimethyl-2H-chromen-6-yl)methyl]propan-2-amine (8a)

7a (102 mg, 0.54 mmol) was dissolved in 2 mL of anhydrous methylene chloride, to which p-toluenesulfonic acid monohydrate (20 mg, 0.1 mmol) and propan-2-amine (1 mL, 12 mmol) were added. The reaction mixture was refluxed overnight and then concentrated in vacuo. The NMR of the crude product confirmed a complete conversion of the aldehyde, 7a, to the corresponding imine by disappearance of the aldehyde proton peak, 9.83 ppm (s, 1H), and appearance of the imine proton peak, 8.19 ppm (s, 1H).

The crude imine was suspended in 3 mL of toluene, to which 1 M diisobutylaluminum hydride in toluene (DIBAL, 2.5 mL, 2.5 mmol) was added slowly to control vigorous bubbling. The reaction mixture was stirred overnight at room temperature, and then 20 mL of 1 N aqueous hydrochloric acid was added to the reaction mixture slowly, to quench the reduction. The resulting emulsion was basified with concentrated aqueous sodium carbonate solution. The reaction mixture was extracted with ethyl acetate (20 mL×3). The combined organic phase was washed with brine, dried with anhydrous magnesium sulfate, and then concentrated in vacuo. 8a was purified by silica gel chromatography with triethylamine/methanol/methylene chloride (1/1/100) as a viscous oil (111 mg, 89% in two steps). $^1$H NMR (CDCl$_3$): δ 1.1 (d, J=6.15 Hz, 6H), 1.4 (s, 6H), 2.85 (septet, J=6.45 Hz, 1H), 3.66 (s, 2H), 5.6 (d, J=9.96 Hz, 1H), 6.3 (d, J=9.67 Hz, 1H), 6.72 (d, J=8.2 Hz, 1H), 6.95 (d, J=2.05 Hz, 1H), 7.04 (dd, J=2.34, 7.91 Hz, 1H).

Other amines (8b-8g) were synthesized by the same method as 8a. The imine formation was confirmed by disappearance of the aldehyde proton peak [9.83 ppm (7a) or 9.81 ppm (7b)] and appearance of the corresponding imine peak [8.1-8.3 ppm (s, 1H)]. The amines were synthesized by reduction of the corresponding imines.

N-[(2,2-Dimethyl-2H-chromen-6-yl)methyl]cyclopropanamine (8b)

Yield=37% in two steps. $^1$H NMR (CDCl$_3$): δ 0.93 (t, J=7.33 Hz, 2H), 1.43 (s, 6H), 1.56 (sextet, J=7.33 Hz, 1H), 2.61 (t, J=7.33 Hz, 2H), 3.70 (s, 2H), 5.61 (d, J=9.67 Hz, 1H), 6.31 (d, J=9.67 Hz, 1H), 6.73 (d, J=8.20 Hz, 1H), 6.97 (d, J=2.05 Hz, 1H), 7.06 (dd, J=2.05, 8.20 Hz, 1H).

N-[(2,2-Dimethyl-2H-chromen-6-yl)methyl]-2-methylpropan-1-amine (8c)

Yield=30% in two steps. $^1$H NMR (CDCl$_3$): δ 0.92 (d, J=6.45 Hz, 6H), 1.43 (s, 6H), 1.79 (septet, J=6.45, 6.74 Hz, 1H), 2.44 (d, J=7.03 Hz, 2H), 3.68 (s, 2H), 5.61 (d, J=9.96 Hz, 1H), 6.32 (d, J=9.96 Hz, 1H), 6.73 (d, J=8.20 Hz, 1H), 6.96 (d, J=2.05 Hz, 1H), 7.05 (dd, J=2.05, 7.91 Hz, 1H).

1-Cyclopropyl-N-[(2,2-dimethyl-2H-chromen-6-yl)methyl]methamine (8d)

Yield=77% in two steps. $^1$H NMR (CDCl$_3$): δ 0.13 (m, 2H), 0.47-0.53 (m, 2H), 0.97-1.05 (m, 1H), 1.42 (s, 6H), 2.51 (d, J=6.74 Hz, 2H), 3.73 (s, 2H), 5.61 (d, J=9.67 Hz, 1H), 6.32 (d, J=9.67 Hz, 1H), 6.73 (d, J=8.20 Hz, 1H), 6.98 (d, J=2.05 Hz, 1H), 7.07 (dd, J=2.05, 8.20 Hz, 1H).

N-[(2,2-Dimethyl-2H-chromen-6-yl)methyl]cyclobutanamine (8e)

Yield=60% in two steps. $^1$H NMR (CDCl$_3$): δ 1.42 (s, 6H), 1.59-1.75 (m, 5H), 2.19-2.27 (m, 2H), 3.25-3.35 (m, 1H), 3.60 (s, 2H), 5.60 (d, J=9.67 Hz, 1H), 6.31 (d, J=9.67 Hz, 1H), 6.72 (d, J=8.20 Hz, 1H), 6.95 (d, J=2.05 Hz, 1H), 7.04 (dd, J=2.05, 8.20 Hz, 1H).

N-[(2,2-Dimethyl-2H-chromen-6-yl)methyl]cyclopentanamine (8l)

Yield=67% in two steps. $^1$H NMR (CDCl$_3$): δ 1.36-1.42 (m, 3H), 1.42 (s, 6H), 1.51-1.56 (m, 2H), 1.68-1.73 (m, 2H), 1.84-1.89 (m, 2H), 3.12 (quintet, J=6.74 Hz, 1H), 3.67 (s, 2H), 5.60 (d, J=9.67 Hz, 1H), 6.31 (d, J=9.96 Hz, 1H), 6.72 (d, J=8.20 Hz, 1H), 6.96 (d, J=2.05 Hz, 1H), 7.05 (dd, J=2.05, 8.20 Hz, 1H).

N-[8-Methoxy-(2,2-dimethyl-2H-chromen-6-yl)methyl]propan-2-amine (8g)

Yield=39% in two steps. $^1$H NMR (CDCl$_3$): δ 1.11 (d, J=6.15 Hz, 6H), 1.46 (s, 6H), 2.88 (septet, J=6.15 Hz, 1H), 3.68 (s, 2H), 3.86 (s, 3H), 5.61 (d, J=9.67 Hz, 1H), 6.28 (d, J=9.96 Hz, 1H), 6.60 (s, 1H), 6.78 (s, 1H).

N-[(2,2-Dimethyl-2H-chromen-6-yl)methyl]-N-(propan-2-yl)pyridine-2-sulfonamide (6a)

Pyridine-2-sulfonyl Chloride

2-Mercaptopyridine (126 mg, 1 mmol) was dissolved in 5 mL of concentrated sulfuric acid to form a yellow solution, which was cooled to around −15° C. with a sodium chloride/ice (1/3) bath. Aqueous sodium hypochlorite solution (10-15%, 11 mL, 15-20 mmol) was added to the solution slowly enough to maintain the internal temperature of the reaction mixture below 10° C., with vigorous stirring. The reaction mixture was stirred at 0° C. for 1 hour and then 10 mL of water was added, which was then extracted with methylene chloride (20 mL×3). The combined organic phase was washed with water, dried with anhydrous magnesium sulfate, and then concentrated in vacuo. Pyridine-2-sulfonyl chloride (145 mg, 72%) was produced as a yellowish viscous liquid. $^1$H NMR (CDCl$_3$): δ 7.684-7.729 (m, 1H), 8.043-8.143 (m, 2H), 8.84 (d, J=4.10 Hz, 1H).

Freshly prepared pyridine-2-sulfonyl chloride (100 mg, 0.6 mmol) was added to a solution of 8a (25 mg, 0.1 mmol) and triethylamine (0.5 mL, 3.6 mmol) in 0.8 mL of methylene chloride. The reaction mixture was refluxed overnight and then concentrated in vacuo. 6a (31 mg, 77%) was purified by silica gel chromatography with ethyl acetate/hexane (1/1). $^1$H NMR (CDCl$_3$): δ 1.03 (d, J=6.74 Hz, 6H), 1.42 (s, 6H), 4.27 (septet, J=6.74 Hz, 1H), 4.45 (s, 2H), 5.61 (d, J=9.67 Hz, 1H), 6.30 (d, J=9.67 Hz, 1H), 6.68 (d, J=8.21 Hz, 1H), 7.04 (d, J=2.05 Hz, 8.20 Hz, 1H), 7.10 (dd, J=2.05, 8.20 Hz, 1H), 7.38-7.47 (m, 1H), 7.81-7.96 (m, 2H), 8.7 (d, J=4.40 Hz, 1H). HRMS (m/z): [M+Na]$^+$ calcd 395.13999, found 395.14017. HPLC-1: $t_R$=4.5 min, purity=98%. HPLC-2: $t_R$=6.5 min, purity=99%.

Other heteroarylsulfonamides containing a pyridine-2-sulfonyl group were synthesized by the same method as that of 6a.

N-Cyclopropyl-N-[(2,2-dimethyl-2H-chromen-6-yl)methyl]pyridine-2-sulfonamide (6b)

Purification was by silica gel chromatography with ethyl acetate/hexane (2/3). Yield=24%. $^1$H NMR (CDCl$_3$): δ 0.725 (t, J=7.33 Hz, 2H), 1.35-1.43 (m, 1H), 3.23 (dd, J=small as broadening of peaks, 7.62 Hz, 2H), 4.44 (s, 2H), 5.61 (d, J=9.96 Hz, 1H), 6.27 (d, J=9.97 Hz, 1H), 6.68 (d, J=8.20 Hz, 1H), 6.93 (d, J=1.76 Hz, 1H), 7.01 (dd, J=2.05, 8.20 Hz, 1H), 7.47 (ddd, J=0.88, 4.69, 7.32 Hz, 1H), 7.85-7.99 (m, 2H), 8.70 (d, J=4.69 Hz, 1H). HRMS (m/z): [M+Na]$^+$ calcd 393.12488, found 395.14008. HPLC-1: $t_R$=5.1 min, purity=100%. HPLC-2: $t_R$=6.8 min, purity=97%.

N-[(2,2-Dimethyl-2H-chromen-6-yl)methyl]-N-(2-methylpropyl)pyridine-2-sulfonamide (6c)

Purification was by silica gel chromatography with ethyl acetate/hexane (1/4). Yield=60%. $^1$H NMR (CDCl$_3$): δ 0.76 (d, J=6.74 Hz, 6H), 1.42 (s, 6H), 1.74 (septet, J=7.03 Hz, 1H), 3.11 (d, J=7.325 Hz, 2H), 4.42 (s, 2H), 5.60 (d, J=9.67 Hz, 1H), 6.24 (d, J=9.67 Hz, 1H), 6.65 (d, J=8.20 Hz, 1H), 6.87 (d, J=2.05 Hz, 1H), 6.96 (dd, J=2.05, 8.20 Hz, 1H), 7.45 (ddd, J=1.17, 4.69, 7.62 Hz, 1H), 7.865 (td, J=1.76, 7.62 Hz, 1H), 7.95 (d, J=7.62 Hz, 1H), 8.69 (d, J=4.69 Hz, 1H). HRMS (m/z): [M+Na]$^+$ calcd 409.15564, found 409.15649. HPLC-1: $t_R$=6.8 min, purity=100%. HPLC-2: $t_R$=8.4 min, purity=97%.

N-(Cyclopropylmethyl)-N-[(2,2-dimethyl-2H-chromen-6-yl)methyl]pyridine-2-sulfonamide (6d)

Purification was by silica gel chromatography with ethyl acetate/hexane (1/2). Yield=24%. $^1$H NMR (CDCl$_3$): δ 0.0115 (d, J=5.27 Hz, 2H), 0.301 (d, J=7.62 Hz, 2H), 0.67-0.825 (m, 1H), 1.425 (s, 6H), 3.17 (d, J=6.74 Hz, 2H), 4.58 (s, 2H), 5.61 (d, J=9.67 Hz, 1H), 6.28 (d, J=9.67 Hz, 1H), 6.69 (d, J=8.21 Hz, 1H), 6.975 (s, 1H), 7.04 (d, J=7.91 Hz, 1H), 7.47 (dd, J=4.98, 7.62 Hz, 1H), 7.88 (t, J=7.62 Hz, 1H), 7.99 (d, J=7.62 Hz, 1H), 8.71 (d, J=4.69 Hz, 1H). HRMS (m/z): [M+Na]$^+$ calcd 407.13999, found 407.14046. HPLC-1: $t_R$=5.7 min, purity=100%. HPLC-2: $t_R$=7.5 min, purity=95%.

N-(Cyclobutyl)-N-[(2,2-dimethyl-2H-chromen-6-yl)methyl]pyridine-2-sulfonamide (6e)

Purification was by silica gel chromatography with ethyl acetate/hexane (1/2). Yield=65%. $^1$H NMR (CDCl$_3$): δ 1.42 (s, 6H), 1.42-2.04 (m, 6H), 4.31-4.39 (m, 1H), 4.51 (s, 2H), 5.61 (d, J=9.96 Hz, 1H), 6.30 (d, J=9.67 Hz, 1H), 6.69 (d, J=8.20 Hz, 1H), 7.00 (s, 1H), 7.06 (dd, J=2.05, 8.205 Hz, 1H), 7.43-7.48 (m, 1H), 7.82-7.94 (m, 2H), 8.69 (d, J=3.81 Hz, 1H). HRMS (m/z): [M+Na]$^+$ calcd 407.13999, found 407.14034. HPLC-1: $t_R$=5.6 min, purity=100%. HPLC-2: $t_R$=7.1 min, purity=96%.

N-(Cyclopentyl)-N-[(2,2-dimethyl-2H-chromen-6-yl)methyl]pyridine-2-sulfonamide (6f)

Purification was by silica gel chromatography with ethyl acetate/hexane (1/4). Yield=16%. $^1$H NMR (CDCl$_3$): δ 1.26-1.59 (m, 8H), 1.43 (s, 6H), 4.31-4.40 (m, 1H), 4.48 (s, 2H), 5.61 (d, J=9.67 Hz, 1H), 6.30 (d, J=9.67 Hz, 1H), 6.69 (d, J=8.21 Hz, 1H), 7.03 (s, 1H), 7.07 (d, J=8.50 Hz, 1H), 7.44-7.48 (m, 1H), 7.83-7.94 (m, 2H), 8.71 (d, J=4.69 Hz, 1H). HRMS (m/z): [M+Na]$^+$ calcd 421.15564, found 421.15577. HPLC-1: $t_R$=7.3 min, purity=100%. HPLC-2: $t_R$=8.4 min, purity=96%.

N-[(8-Methoxy-2,2-dimethyl-2H-chromen-6-yl)methyl]pyridine-2-sulfonamide (6g)

Purification was by silica gel chromatography with ethyl acetate/hexane (2/1). Yield=23%. $^1$H NMR (CDCl$_3$): δ 1.05 (d, J=6.74 Hz, 6H), 1.47 (s, 6H), 3.84 (s, 3H), 4.27 (septet, J=6.74 Hz, 1H), 4.45 (s, 2H), 5.61 (d, J=9.96 Hz, 1H), 6.27 (d, J=9.96 Hz, 1H), 6.62 (s, 1H), 6.88 (s, 1H), 7.43-7.48 (m, 1H), 7.82-7.93 (m, 2H), 8.70 (d, J=4.40 Hz, 1H). HRMS (m/z): [M+Na]$^+$ calcd 425.15055, found 425.15089. HPLC-1: flow rate 2 mL/min, $t_R$=2.9 min, purity=97%; flow rate 1 mL/min, $t_R$=5.6 min, purity=99%. HPLC-2: $t_R$=5.1 min, purity=100%.

N-[(2,2-Dimethyl-2H-chromen-6-yl)methyl]-N-(2-methylpropyl)pyridine-4-sulfonamide (6i)

Pyridine-4-sulfonyl Chloride

Pyridine-4-sulfonyl, 1,3-thiazole-2-sulfonyl, and 1-methyl-1H-imidazole-2-sulfonyl chloride were synthesized by the same method as that of pyridine-2-sulfonyl chloride. They were used immediately after synthesis due to their instabilities at temperatures above 0° C. Ten theoretical equivalents of the sulfonyl chloride were synthesized, which were extracted with 10 mL of cold methylene chloride, washed with cold brine, and then dried with anhydrous magnesium sulfate. The sulfonyl chloride solution in methylene chloride was immersed in ice-water bath and concentrated with argon flow until the volume was reduced to 3 mL.

8a (25 mg, 0.1 mmol) was dissolved in 0.8 mL of methylene chloride, to which 0.5 mL of N,N-diisopropylethylamine (DIEA, 0.5 mL, 3 mmol) was added and cooled to 0° C. Ten equivalents of freshly prepared pyridine-4-sulfonyl chloride was added to the reaction mixture slowly, which was stirred at 0° C. for 3 h with slow argon flow. 6i (25 mg, 63%) was purified by silica gel chromatography with ethyl acetate/hexane (1/5). $^1$H NMR (CDCl$_3$): δ 0.78 (d, J=6.74 Hz, 6H), 1.43 (s, 6H), 1.72-1.82 (m, 1H), 2.96 (d, J=7.62 Hz, 2H), 4.27 (s, 2H), 5.62 (d, J=9.96 Hz, 1H), 6.21 (d, J=9.96 Hz, 1H), 6.68 (d, J=7.91 Hz, 1H), 6.77 (d, J=2.05 Hz, 1H), 6.91 (dd, J=2.05, 8.50 Hz, 1H), 7.63 (d, J=5.86 Hz, 1H), 8.82 (d, J=6.15 Hz, 1H). HRMS (m/z): [M+Na]$^+$ calcd 386.16641, found 387.17447. HPLC-1: $t_R$=6.5 min, purity=98%. HPLC-2: $t_R$=8.4 min, purity=96%.

6j and 6k were synthesized by the same method as 6i.

N-[(2,2-Dimethyl-2H-chromen-6-yl)methyl]-N-(2-methylpropyl)-1-methyl-1H-imidazole-2-sulfonamide (6j)

Purification was by silica gel chromatography with ethyl acetate/hexane (1/2). Yield=58%. $^1$H NMR (CDCl$_3$): δ 0.77 (d, J=6.45 Hz, 6H), 1.43 (s, 6H), 1.63-1.70 (m, 1H), 3.20 (d, J=7.62 Hz, 1H), 3.90 (s, 3H), 4.47 (s, 2H), 5.62 (d, J=9.96 Hz, 1H), 6.29 (d, J=9.67 Hz, 1H), 6.71 (d, J=8.20 Hz, 1H), 6.93-6.94 (m, 2H), 7.04 (dd, J=2.34, 8.20 Hz, 1H), 7.08 (d, J=0.88 Hz, 1H). HRMS (m/z): [M+Na]$^+$ calcd 412.16654, found 412.16699. HPLC-1: $t_R$=5.8 min, purity=100%. HPLC-2: $t_R$=8.7 min, purity=97%.

N-[(2,2-Dimethyl-2H-chromen-6-yl)methyl]-N-(2-methylpropyl)-1,3-thiazole-2-sulfonamide (6k)

Purification was by silica gel chromatography with ethyl acetate/hexane (1/2). Yield=17%. $^1$H NMR (CDCl$_3$): δ 0.79 (d, J=6.45 Hz, 6H), 1.42 (s, 6H), 1.77-1.81 (m, 1H), 3.12 (d, J=7.62 Hz, 2H), 4.43 (s, 2H), 5.62 (d, J=9.96 Hz, 1H), 6.26 (d, J=9.67 Hz, 1H), 6.68 (d, J=8.20 Hz, 1H), 6.87 (d, J=2.34 Hz, 1H), 6.97 (dd, J=2.34, 8.20 Hz, 1H), 7.58 (d, J=3.22 Hz, 1H), 7.95 (d, J=3.22 Hz, 1H). HRMS (m/z): [M+Na]$^+$ calcd 415.11206, found 415.11253. HPLC-1: $t_R$=8.0 min, purity=100%. HPLC-2: $t_R$=10 min, purity=89%.

8-Hydroxy-2,2-dimethyl-2H-chromene-6-carbaldehyde (9)

3,4-Dihydroxybenzaldehyde (2.3 g, 17 mmol) and 3-methylbut-2-enal (1 mL, 10 mmol) were dissolved in 3 mL of pyridine and refluxed overnight. Pyridine was evaporated under vacuum, and the crude reaction mixture was dissolved in methylene chloride. 9 (103 mg, 2.4%) was purified with silica gel chromatography with ethyl acetate/hexane (1/50). $^1$H NMR (CDCl$_3$): δ 1.50 (s, 6H), 5.70 (d, J=10.1 Hz, 1H), 6.38 (d, J=10.1 Hz, 1H), 7.15 (d, J=2.14 Hz, 1H), 7.32 (d, J=1.83 Hz, 1H), 9.78 (s, 1H).

8-(Methoxymethoxy)-2,2-dimethyl-2H-chromene-6-carbaldehyde (10)

Chloromethyl methyl ether (4 mL, 5 mmol) was added to a solution of 9 (103 mg, 0.5 mmol) and N,N-diisopropylethylamine (0.2 mL, 1 mmol) in 4 mL of methylene chloride. The reaction mixture was refluxed overnight and concentrated in vacuo. 10 (48 mg, 38%) was purified with ethyl acetate/hexane (1/50). $^1$H NMR (CDCl$_3$): δ 1.52 (s, 6H), 3.54 (s, 3H), 5.25 (s, 2H), 5.71 (d, J=9.67 Hz, 1H), 6.38 (d, J=9.96 Hz, 1H), 7.26 (d, J=1.76 Hz, 1H), 7.52 (d, J=1.76 Hz, 1H), 9.80 (s, 1H).

N-[(8-Methoxymethoxy-2,2-dimethyl-2H-chromen-6-yl)methyl]-2-methylpropan-1-amine (11)

2-Methylpropan-1-amine (0.5 mL, 5 mmol) and p-toluenesulfonic acid monohydrate (110 mg, 0.6 mmol) were added to a solution of 10 (143 mg, 0.6 mmol) in 5 mL of methylene chloride. The reaction mixture was refluxed overnight and concentrated in vacuo. Disappearance of the aldehyde peak at 9.80 ppm (s, 1H) and appearance of the imine peak at 8.07 ppm (s, 1H) were confirmed by NMR.

The crude product was dissolved in 3 mL of a mixture of methylene chloride and toluene [1/2 (v/v)], to which 1 M DIBAL in toluene (3 mL, 3 mmol) was added slowly to generate gentle bubbling. The reaction mixture was stirred for 5 h and 20 mL of 1 N aqueous HCl was added. The aqueous phase was extracted by methylene chloride (40 mL×3). The combined organic layer was washed by brine, dried with magnesium sulfate, and then concentrated in vacuo.

11 (22 mg, 13%) was purified by silica gel chromatography with triethylamine/methanol/methylene chloride (1/3/100). $^1$H NMR (CDCl$_3$): δ 0.91 (d, J=3.13 Hz, 6H), 1.46 (s, 6H), 1.75-1.82 (m, 1H), 2.43 (d, J=7.04 Hz, 2H), 3.53 (s, 3H), 3.66 (s, 2H), 5.20 (s, 2H), 5.62 (d, J=9.78 Hz, 1H), 6.30 (d, J=9.78 Hz, 1H), 6.69 (d, J=1.96 Hz, 1H), 6.96 (d, J=1.96 Hz, 1H).

N-[(8-Hydroxy-2,2-dimethyl-2H-chromen-6-yl)methyl]-N-(propan-2-yl)pyridine-2-sulfonamide (6h)

11 (30 mg, 0.1 mmol), pyridine-2-sulfonyl chloride (57 mg, 0.3 mmol), and N,N-diisopropylethylamine (0.2 mL, 1 mmol) were dissolved in 1 mL of methylene chloride and stirred at room temperature overnight. A completion of the reaction was confirmed by disappearance of the amine spot by TLC with triethylamine/methanol/methylene chloride (1/3/100) and appearance of the product spot by TLC with ethyl acetate/hexane (1/1). N-[(8-Methoxymethoxy-2,2-dimethyl-2H-chromen-6-yl)methyl]-N-(propan-2-yl)pyridine-2-sulfonamide (31 mg, 70%) was purified by silica gel chromatography with ethyl acetate/hexane (1/1). $^1$H NMR (CDCl$_3$): δ 0.78 (d, J=6.45 Hz, 6H), 1.45 (s, 6H), 1.72-1.76 (m, 1H), 3.11 (d, J=7.62 Hz, 2H), 3.50 (s, 3H), 4.40 (s, 2H), 5.14 (s, 2H), 5.62 (d, J=9.96 Hz, 1H), 6.23 (d, J=9.67 Hz, 1H), 6.60 (d, J=1.76 Hz, 1H), 6.87 (d, J=1.76 Hz, 1H), 7.43-7.47 (m, 1H), 7.84-7.96 (m, 2H), 8.68-8.7 (m, 1H).

N-[(8-Methoxymethoxy-2,2-dimethyl-2H-chromen-6-yl)methyl]-N-(propan-2-yl)pyridine-2-sulfonamide (31 mg, 0.07 mmol) was dissolved in a cosolvent of tetrahydrofuran (1 mL) and 6 N aqueous HCl (1 mL), and the reaction stirred for 3 h. Ten milliliters of water was added to the reaction mixture, and then tetrahydrofuran was evaporated. The remaining aqueous phase was extracted by methylene chloride (10 mL×3), washed with brine, dried with anhydrous magnesium sulfate, and concentrated in vacuo. 6h (19 mg, 49%) was purified by silica gel chromatography with ethyl acetate/hexane (1/1). $^1$H NMR (CDCl$_3$): δ 0.77 (d, J=6.45 Hz, 6H), 1.44 (s, 6H), 1.72-1.79 (m, 1H), 3.11 (d, J=7.62 Hz, 2H), 4.39 (s, 2H), 5.61 (d, J=9.67 Hz, 1H), 6.25 (d, J=9.96 Hz, 1H), 6.50 (d, J=1.76 Hz, 1H), 6.65 (d, J=1.76 Hz, 1H), 7.43-7.47 (m, 1H), 7.84-7.97 (m, 2H), 8.69 (d, J=4.40 Hz, 1H). HRMS (m/z): [M+Na]$^+$ calcd 425.15055, found 425.15091. HPLC-1: flow rate 2 mL/min, $t_R$=2.9 min, purity=100%; flow rate 1 mL/min, $t_R$=5.6 min, purity=100%. HPLC-2: $t_R$=5.172 min, purity=100%.

N-[(8-Hydroxy-2,2-dimethyl-2H-chromen-6-yl)methyl]-N-(propan-2-yl)pyridine-4-sulfonamide (6l)

6l was synthesized by the same method as 6h. Yield in two steps=48%. $^1$H NMR (CDCl$_3$): δ 0.80 (d, J=6.74 Hz, 6H), 1.45 (s, 6H), 1.75-1.82 (m, 1H), 2.98 (d, J=7.62 Hz, 2H), 4.24 (s, 2H), 5.62 (d, J=9.67 Hz, 1H), 6.22 (d, J=9.67 Hz, 1H), 6.39 (s, 1H), 6.60 (s, 1H), 7.62 (d, J=5.86 Hz, 1H), 8.81 (d, J=4.98 Hz, 1H). HRMS (m/z): [M+Na]$^+$ calcd 402.16133, found 403.16924. HPLC-1: flow rate 2 mL/min, $t_R$=2.7 min, purity=98%; flow rate 1 mL/min, $t_R$=5.3 min, purity=98%. HPLC-2: $t_R$=5.532 min, purity=100%.

Inhibition of HIF Transcriptional Activity

Figure 2:
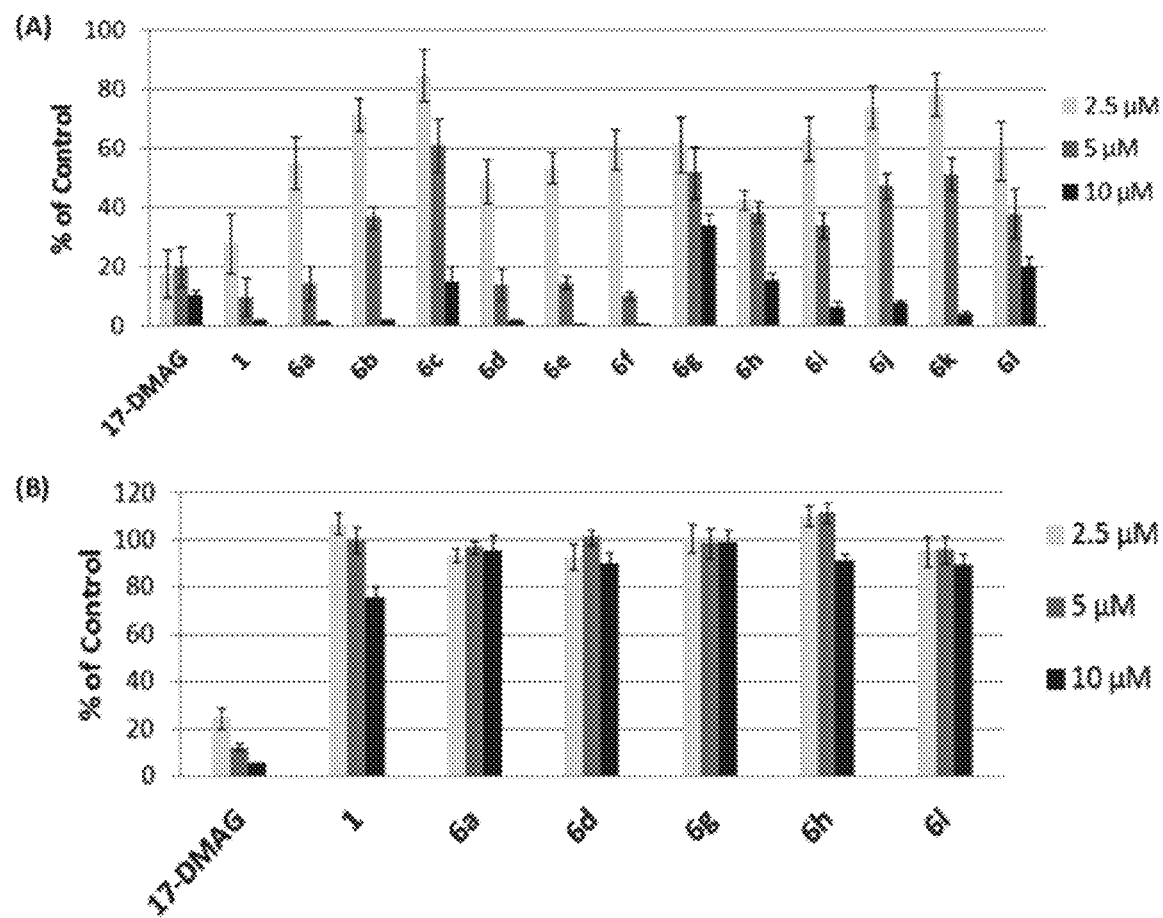
FIG. 2 shows data from Reporter assays measuring luciferase activity in extracts from cells containing hypoxia-inducible (A) or constitutive (B) luciferase reporter genes following treatment with the indicated heteroarylsulfonamides. Results are plotted as percent of luciferase activity found in extracts of untreated cells used as controls. (A) Luciferase activity in extracts of LN229-V6R cells, which contain a HIF-inducible luciferase reporter gene. The cells were grown under hypoxia to activate HIF. (B) Luciferase activity in extracts of LN229-Lux cells, which contain a constitutively expressed luciferase reporter gene. Results shown are from cells grown under normoxia; similar results were obtained under hypoxia.

The effects of the 12 heteroarylsulfonamides on HIF transcriptional activity under hypoxia were measured by determining the luciferase activity present in LN229-V6R cells, which contain a stably integrated hypoxia/HIF inducible luciferase reporter gene. As a control for the absence of inhibition on luciferase enzyme per se, we also tested 1 and five heteroarylsulfonamides in LN229-Lux cells that contain a constitutive luciferase reporter gene driven by a retroviral LTR promoter. An Hsp90 inhibitor, 17-DMAG, and 1 were used as positive controls. 17-DMAG inhibited both reporter cell lines due to its known cytotoxicity; whereas 1 and heteroarylsulfonamides reduced luciferase activity only in LN229-V6R cells under hypoxia. The heteroarylsulfonamides decreased HIF-1 activity in a dose-dependent fashion with $IC_{50}$ values below (6a, 6b, 6d-6f, 6h, 6i, 6l) or close to 5 μM (6c, 6g, 6j, 6k) (FIG. 2). Region 1 of 6c, 6i, 6j, and 6k was diversified with pyridine-2-sulfonyl, pyridine-4-sulfonyl, 1-methyl-1H-imidazole-2-sulfonyl, and thiazole-2-sulfonyl groups, among which the pyridine-4-sulfonyl group of 6i showed the strongest HIF reporter inhibition. However, the pyridine-2-sulfonyl group of 6h showed stronger inhibition than the pyridine-4-sulfonyl group of 6l, when a hydroxyl group replaces the C-8 hydrogen in region 3.

Region 2 of 6a-6f was varied with propan-2-yl, cyclopropyl, 2-methylpropan-1-yl, cyclopropylmethyl, cyclobutyl, and cyclopentyl groups, among which cyclopropylmethyl of 6d showed the strongest HIF reporter inhibition.

Region 3 of 6a and 6g was altered at the C-8 position of the 2,2-dimethyl-2H-chromene ring with a hydrogen and a methoxy group, and 6a (hydrogen) showed the strongest inhibition. Region 3 of 6c and 6i was different at the same position with a hydrogen and a hydroxyl group. In this case, 6i (hydroxyl) showed stronger inhibition at low concentration; however, dose-dependent inhibition increased more sharply for 6c (hydrogen). Region 3 of 6i and 6l was modified in the same way as 6c and 6g with a hydrogen and a hydroxyl group, of which 6l (hydroxyl) showed slightly stronger inhibition at low concentration; however, dose-dependent inhibition increased more sharply for 6l (hydrogen).

Effect on HIF-1α Stability Under Hypoxia

Figure 3:
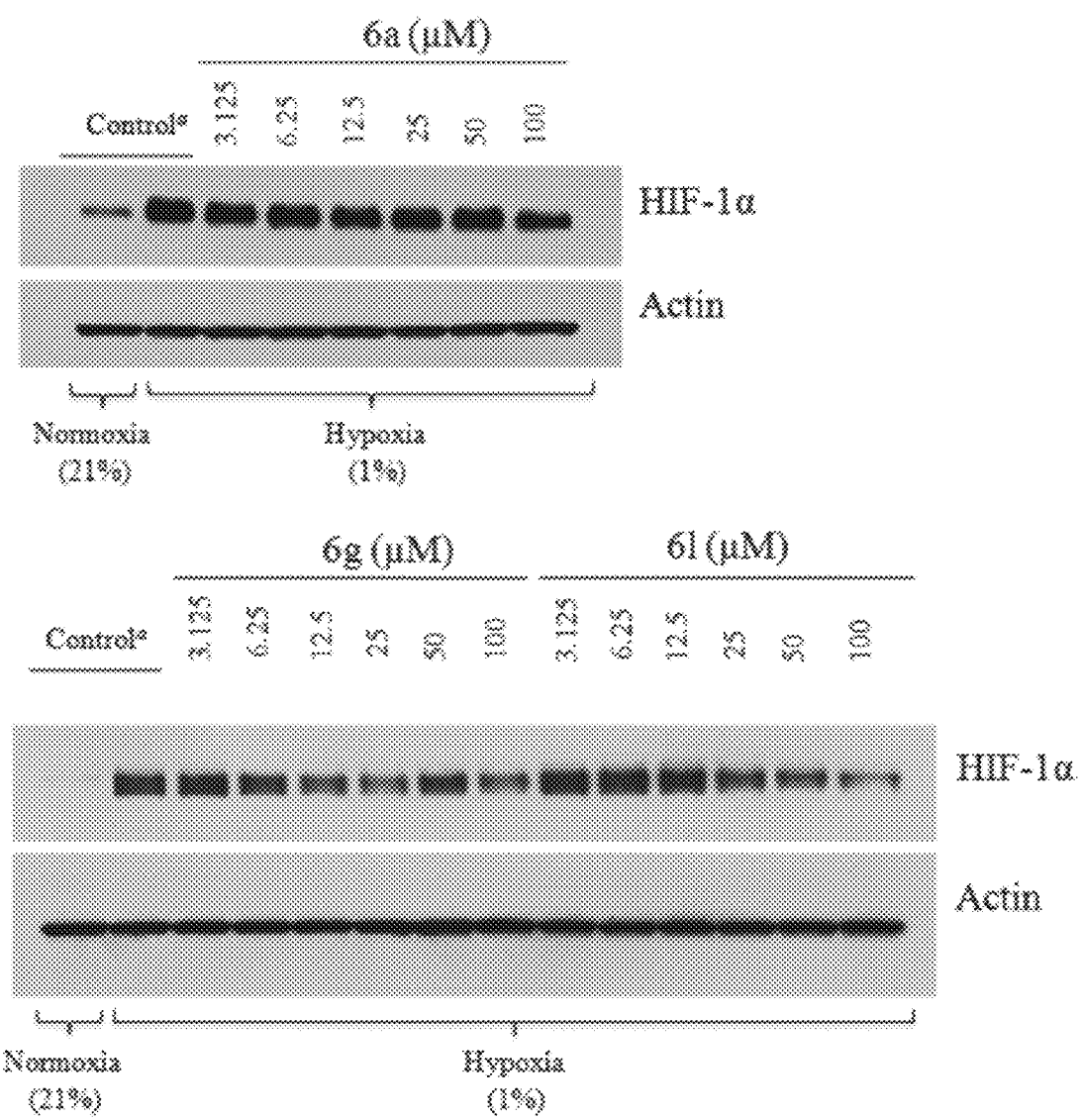
FIG. 3 shows data on the measurement of HIF-1α levels in LN229-V6R cells in response to various doses of 6a, 6g, and 6l by Western blot analysis. $^a$Controls contain vehicle only (1% DMSO).

HIF-1 is a heterodimer of HIF-1α and HIF-1β subunits, which then associates with p300 or CBP cofactors to form an active transcriptional complex. We previously demonstrated that in contrast to many prior HIF inhibitors, 1 does not antagonize hypoxia-induced HIF-1α expression under concentrations at which it blocks HIF transcription in the reporter assay. To determine whether the heteroarylsulfonamides retain this property, we determined the levels of HIF-1α protein under hypoxia in LN229-V6R cells. For these experiments we selected 6a, 6g, and 6l because the three compounds exhibited different degrees of HRE reporter inhibition and possess structural diversities at the C-8 position of the chromene ring. We investigated if the levels of HIF-1α protein would correlate with transcriptional inhibition of the HRE reporter by the compounds. LN229-V6R cells were treated with the compounds at concentrations of 3, 6, 12, 25, 50, and 100 μM under hypoxia for 24 h, and then HIF-1α protein levels in the cell extracts were examined by Western blotting. 6a had no effect on HIF-1α levels at all concentrations tested, except for a slight reduction at the highest concentration (100 μM). 6g and 6l decreased HIF-1a levels in a dose-dependent fashion starting from 12 and 25 μM, respectively (FIG. 3). In comparison, in the above HRE-mediated luciferase assays HIF-1 transcriptional activity was inhibited completely by 6a and by more than 60-80% by 6g and 6l when tested at 10 μM (FIG. 2). These results indicate that 6a, 6g, and 6l most likely inhibit HIF transcription in a protein stability independent way similar to 1. The reduction in HIF-1α levels afforded by all three compounds at 100 μM may reflect nonspecific cytotoxicity.

Physicochemical Properties and Metabolic Stability

Experimental determinations of log $P_{7.4}$, aqueous solubility, and metabolic stability of a selected number of the heteroarylsulfonamides were performed to further characterize the compounds (Table 2 log $P_{7.4}$ was measured by either the shake flask method (6a, 6g) or the HPLC method (1, 6b-6f, 6h-6l) according to OECD guidelines. Most compounds followed the trends predicted by in silico calculations, and the measured values were smaller than the predicted values by 1.0-1.5. When a methoxy group or hydroxyl group is placed at the C-8 position of the chromene ring instead of a hydrogen, as in 6g, 6h, and 6l, the log $P_{7.4}$ value decreased by more than 2 from the predicted values to result in 1.2-1.3. The presence of a 2-methylpropan-2-yl group in region 2 conferred high log $P_{7.4}$ values, and heteroarylsulfonyl groups in region 1 also affected log $P_{7.4}$ values, as shown for 6c, 6i, 6j, and 6k.

Aqueous solubilities of 1, 6a, 6d, and 6g were quantified by HPLC coupled with a UV detector on saturated aqueous suspensions after filtration with a polytetrafluoroethylene (PTFE) filter (pore size 0.2 μm). 6a and 6d were chosen due to their strong activity in the HRE-reporter assay, and 6g was picked to evaluate the influence of the methoxy group attached to the C-8 position of the chromene ring. Aqueous solubilities of 6a, 6d, and 6g are, respectively, 100, 20, and 9000 times better than that of 1, which are consistent with the log $S_w$ predictions for 6a and 6d. The substitution of hydrogen with a methoxy group at the C-8 position of the chromene ring increased the aqueous solubility by 90 times (compare 6a and 6g). Additional measurements of aqueous solubility of 1 and 6a were performed by laser nephelometry at three different pHs (3.0, 5.0, and 7.4). pH did not affect aqueous solubility of 1; however, low pH increased the aqueous solubility of 6a by 50-60 times (pH 5.0, pH 3.0) due to the presence of the basic nitrogen in the pyridin-2-sulfonyl group in region 1.

Metabolic stabilities of 1, 6a, 6d, 6g, and 6l were measured in mouse plasma and homogenates of mouse liver in PBS [1:2 (w/v)]. The concentrations of all compounds did not decrease by more than 1% when the compounds were incubated in mouse plasma at 37° C. for 24 h, which indicated the absence of degradation or metabolism in plasma. All compounds underwent ex vivo hepatic metabolism with the half-lives shown in Table 2, in which 1 showed the fastest and 6a the slowest metabolism.

Inhibition of Cell Viability/Proliferation

To determine whether 6a, 6g, and 6l altered tumor cell growth in culture, we performed sulforhodamine B (SRB) assays in LN229-V6R glioma cells in 3 days, and to further examine the cell growth inhibitory activity of 6a, 6g, and 6l in an independent biological assay, we performed clonogenicity assays in LN229 human glioblastoma cells and HFF-1 immortalized human fibroblasts, over a period of 14 days. $IC_{50}$ values (μM) of SRB and clonogenicity assays are presented in Table 3.

Sulforhodamine B (SRB) Assay

LN229-V6R cells ($5 \times 10^3$ cells/well) were seeded and cultured under normoxia for 24 h, and cell densities were measured. The cells were then treated with serially diluted 6a, 6g, and 6l (1.56-100 μM; 1% DMSO final in culture medium) under normoxia or hypoxia for 72 h. The three heteroarylsulfonamides showed stronger cytotoxicity under normoxia than under hypoxia. The $IC_{50}$ values of cytotoxicity of the three heteroarylsulfonamides under hypoxia were over 100 μM in 3 days, whereas all of them decreased HRE-reporter activity by 60-95% at 10 μM in 1 day.

Clonogenicity Assays 6a, 6g, and 6l showed stronger inhibition of cell proliferation under normoxia than under hypoxia in both of glioblastoma and fibroblast cell lines, which was similar to results of SRB assays. The cytotoxicity profiles of each compound against glioblastoma (LN229) and fibroblast (HFF-1) cell lines were similar, suggesting nonspecific cytotoxicities. 61 displayed the strongest cytotoxicity in both of the two cell lines.

TABLE 1

Molecular Weights (Mw) and log P and log Sw Values of 3,4-Dimethoxy-N-[(2,2-dimethyl-2H-chromene-6-yl)methyl]-N-phenylbenzenesulfonamide (1), N-[(2,2-Dimethyl-2H-chromen-6-yl)methyl]-N-(propan-2-yl)arylsulfonamides (2,3,4,5), and Twelve N-Alkyl-N-[(8-R-2,2-dimethyl-2H-chromen-6-yl)methyl]heteroarylsulfonamides by in Silico Calculations

| Compound Name | Chemical Structure | $M_w$ (Molecular Weight) | log P (Lipophilicity) | log $S_w$ (Aqueous Solubility) |
|---|---|---|---|---|
| 1 | 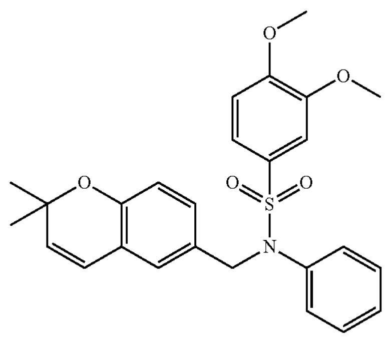 | 465.61 | 4.94 | −6.05 |
| 2 | 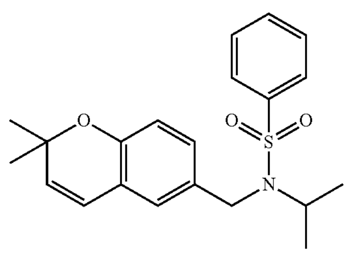 [SMILES: CC(C)N(Cc1ccc2c(c1)C=CC(C)(C)O2)S(=O)(=O)c1ccccc1] | 371.54 | 4.37 | −4.78 |
| 3 | 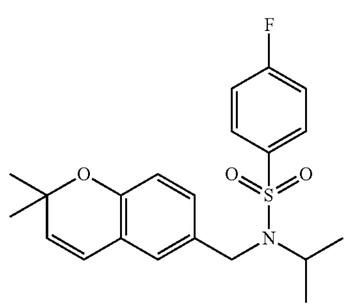 [SMILES: CC(C)N(Cc1ccc2c(c1)C=CC(C)(C)O2)S(=O)(=O)c1ccc(F)cc1] | 389.53 | 4.56 | −4.79 |
| 4 | 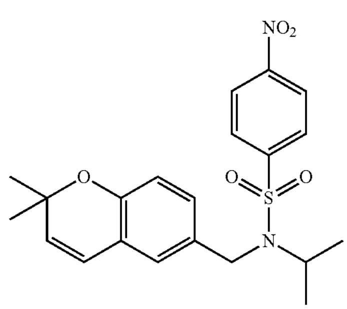 [SMILES: CC(C)N(Cc1ccc2c(c1)C=CC(C)(C)O2)S(=O)(=O)c1ccc([N+](=O)[O-])cc1] | 416.54 | 4.31 | −5.07 |

TABLE 1-continued

Molecular Weights (Mw) and log P and log Sw Values of 3,4-Dimethoxy-N-[(2,2-dimethyl-2H-chromene-6-yl)methyl]-N-phenylbenzenesulfonamide (1), N-[(2,2-Dimethyl-2H-chromen-6-yl)methyl]-N-(propan-2-yl)arylsulfonamides (2,3,4,5), and Twelve N-Alkyl-N-[(8-R-2,2-dimethyl-2H-chromen-6-yl)methyl]heteroarylsulfonamides by in Silico Calculations

| Compound Name | Chemical Structure | $M_w$ (Molecular Weight) | log P (Lipophilicity) | log $S_w$ (Aqueous Solubility) |
|---|---|---|---|---|
| 5 | 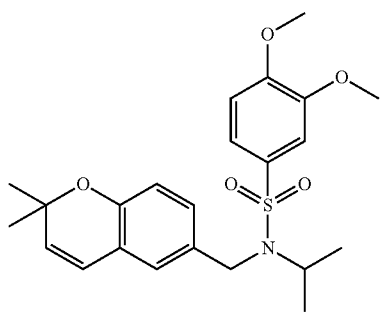 | 431.60 | 4.13 | −4.81 |
| 6a | 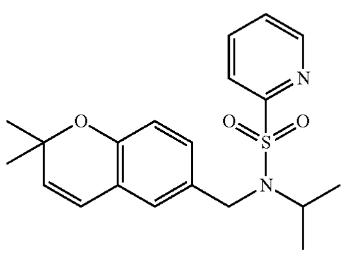 [SMILES: CC(C)N(Cc1ccc2c(c1)C=CC(C)(C)O2)S(=O)(=O)c1ccccn1] | 372.53 | 3.64 | −3.73 |
| 6b | 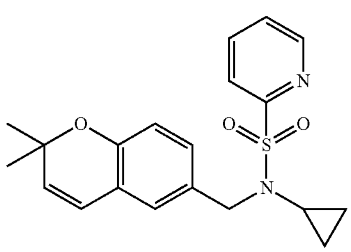 [SMILES: CC1(C)C=Cc2cc(CN(C3CC3)S(=O)(=O)c3ccccn3)ccc2O1] | 370.51 | 3.42 | −3.89 |
| 6c | 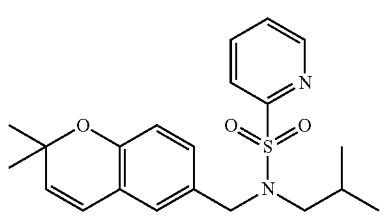 [SMILES: CC(C)CN(Cc1ccc2c(c1)C=CC(C)(C)O2)S(=O)(=O)c1ccccn1] | 386.56 | 4.03 | −3.91 |
| 6d | 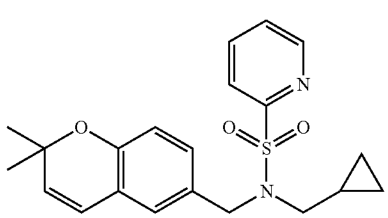 [SMILES: CC1(C)C=Cc2cc(CN(CC3CC3)S(=O)(=O)c3ccccn3)ccc2O1] | 384.54 | 3.75 | −4.11 |

TABLE 1-continued

Molecular Weights (Mw) and log P and log Sw Values of 3,4-Dimethoxy-N-[(2,2-dimethyl-2H-chromene-6-yl)methyl]-N-phenylbenzenesulfonamide (1), N-[(2,2-Dimethyl-2H-chromen-6-yl)methyl]-N-(propan-2-yl)arylsulfonamides (2,3,4,5), and Twelve N-Alkyl-N-[(8-R-2,2-dimethyl-2H-chromen-6-yl)methyl]heteroarylsulfonamides by in Silico Calculations

| Compound Name | Chemical Structure | $M_w$ (Molecular Weight) | log P (Lipophilicity) | log $S_w$ (Aqueous Solubility) |
|---|---|---|---|---|
| 6e | 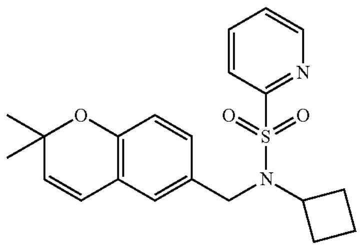 [SMILES: CC1(C)C=Cc2cc(CN(C3CCC3)S(=O)(=O)c3ccccn3)ccc2O1] | 384.54 | 3.77 | −3.94 |
| 6f | 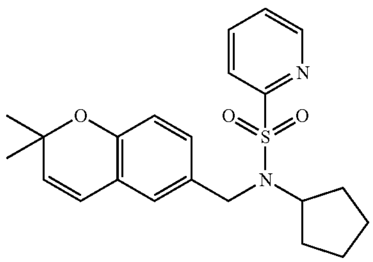 [SMILES: CC1(C)C=Cc2cc(CN(C3CCCC3)S(=O)(=O)c3ccccn3)ccc2O1] | 398.57 | 4.18 | −4.20 |
| 6g | 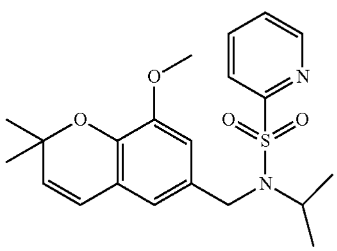 [SMILES: COc1cc(CN(C(C)C)S(=O)(=O)c2ccccn2)cc2c1OC(C)(C)C=C2] | 402.56 | 3.54 | −3.74 |
| 6h | 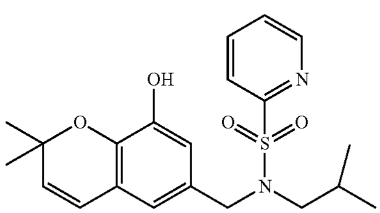 [SMILES: CC(C)CN(Cc1cc(O)c2c(c1)C=CC(C)(C)O2)S(=O)(=O)c1ccccn1] | 402.56 | 3.59 | −3.45 |
| 6i | 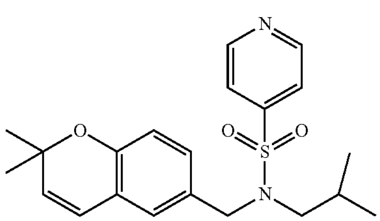 [SMILES: CC(C)CN(Cc1ccc2c(c1)C=CC(C)(C)O2)S(=O)(=O)c1ccncc1] | 386.56 | 3.78 | −3.95 |
| 6j | 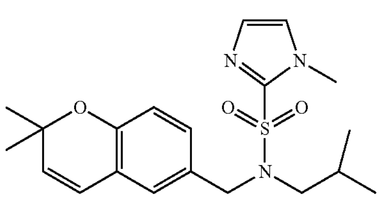 [SMILES: CC(C)CN(Cc1ccc2c(c1)C=CC(C)(C)O2)S(=O)(=O)c1nccn1C] | 389.57 | 3.45 | −3.16 |

TABLE 1-continued

Molecular Weights (Mw) and log P and log Sw Values of 3,4-Dimethoxy-N-[(2,2-dimethyl-2H-chromene-6-yl)methyl]-N-phenylbenzenesulfonamide (1), N-[(2,2-Dimethyl-2H-chromen-6-yl)methyl]-N-(propan-2-yl)arylsulfonamides (2,3,4,5), and Twelve N-Alkyl-N-[(8-R-2,2-dimethyl-2H-chromen-6-yl)methyl]heteroarylsulfonamides by in Silico Calculations

| Compound Name | Chemical Structure | $M_w$ (Molecular Weight) | log P (Lipophilicity) | log $S_w$ (Aqueous Solubility) |
|---|---|---|---|---|
| 6k | 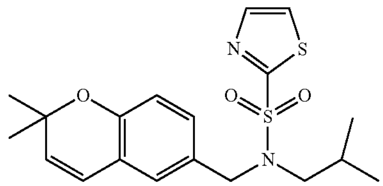 [SMILES: CC(C)CN(Cc1ccc2c(c1)C=CC(C)(C)O2)S(=O)(=O)c1nccs1] | 392.59 | 4.08 | −4.19 |
| 6l | 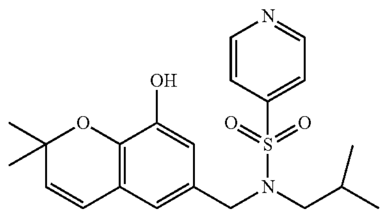 [SMILES: CC(C)CN(Cc1cc(O)c2c(c1)C=CC(C)(C)O2)S(=O)(=O)c1ccncc1] | 402.56 | 3.37 | −3.39 |

TABLE 2 log $P_{7.4}$, Aqueous Solubility, and Hepatic Metabolic Stability of N-Alkyl-N-[(8-R-2,2-dimethyl-2H-chromen-6-yl)methyl]heteroarylsulfonamides

| compd | log $P_{7.4}$ | aqueous solubility (n = 3) (μg/mL, μM) | half-lif[b] (h) | remaining HIF-1 activity at 2.5 μM % of control | rank |
|---|---|---|---|---|---|
| 1 | 3.7 | 0.003[a] ± 0.001, 0.009 ± 0.003 | 11 | 18 | 1 |
| 6a | 2.0 | 0.3[a] ± 0.1, 1 ± 0.1 | 20 | 55 | 5 |
| 6b | 3.0 | nd[c] | nd | 71 | 10 |
| 6c | 4.1 | nd | nd | 85 | 13 |
| 6d | 3.1 | 0.1[a] ± 0.02, 0.2 ± 0.07 | 13 | 49 | 3 |
| 6e | 3.0 | nd | nd | 53 | 4 |
| 6f | 3.8 | nd | nd | 60 | 7 |
| 6g | 1.3 | 22 ± 16, 80 ± 36 | 15 | 61 | 8 |
| 6h | 1.3 | nd | 15 | 43 | 2 |
| 6i | 3.6 | nd | nd | 63 | 9 |
| 6j | 3.1 | nd | nd | 74 | 11 |
| 6k | 4.4 | nd | nd | 78 | 12 |
| 6l | 1.2 | nd | nd | 59 | 6 |

TABLE 3

IC$_{50}$ (μM) Values of SRB and Clonogenecity Assays (A) SRB Assay

| compd | condition | IC$_{50}$ (μM) |
|---|---|---|
| 6a | normoxia | 100 |
| | hypoxia | 126 |
| 6g | normoxia | 73 |
| | hypoxia | 146 |
| 6l | normoxia | 92 |
| | hypoxia | 113 |

TABLE 3-continued

IC$_{50}$ (μM) Values of SRB and Clonogenecity Assays (B) Clonogenecity Assays

| compd | cell line | condition | IC$_{50}$ (μM) |
|---|---|---|---|
| 6a | LN229 | normoxia | 82 |
| | | hypoxia | 134 |
| | HFF-1 | normoxia | 62 |
| | | hypoxia | 93 |
| 6g | LN229 | normoxia | 69 |
| | | hypoxia | >100 |
| | HFF-1 | normoxia | 55 |
| | | hypoxia | >100 |
| 6l | LN229 | normoxia | 23 |
| | | hypoxia | 30 |
| | HFF-1 | normoxia | 22 |
| | | hypoxia | 40 |

The invention claimed is:

1. A compound of the formula

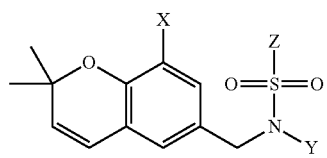

or salts thereof, wherein

X is selected from hydroxy and methoxy, wherein X is optionally substituted with one or more, the same or different $R^1$;

Y is selected from alkyl, isopropyl, and isobutyl wherein Y is optionally substituted with one or more, the same or different $R^1$;

Z is 2-pyridinyl, 4-pyridinyl wherein Z is optionally substituted with one or more, the same or different $R^1$;

$R^1$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^1$ is optionally substituted with one or more, the same or different, R$^2$; and R$^2$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. The compound of claim 1 wherein the compound comprises a carbon 11 or fluorine 18 radionuclide.

3. The compound of claim 1 selected from:
N-((8-hydroxy-2,2-dimethyl-2H-chromen-6-yl)methyl)-N-isobutylpyridine-4-sulfonamide;
N-((8-hydroxy-2,2-dimethyl-2H-chromen-6-yl)methyl)-N-isobutylpyridine-2-sulfonamide;
N-[(8-Methoxy-2,2-dimethyl-2H-chromen-6-yl)methyl]-N-(propan-2-yl)pyridine-2-sulfonamide;
N-[(8-Hydroxy-2,2-dimethyl-2H-chromen-6-yl)methyl]-N-(propan-2-yl)pyridine-2-sulfonamide; and
N-[(8-Hydroxy-2,2-dimethyl-2H-chromen-6-yl)methyl]-N-(propan-2-yl)pyridine-4-sulfonamide.

4. A pharmaceutical composition comprising a compound of claim 1 or a pharmaceutically acceptable salt and a pharmaceutically acceptable excipient.

5. A method of treating cancer comprising administering an effective amount of a pharmaceutical composition of claim 4.

6. The method of claim 5, wherein the cancer is selected from glioblastoma (GBM), breast, pancreatic, colon, metastatic lung cancers, bladder cancer, lung cancer, breast cancer, melanoma, colon and rectal cancer, non-hodgkin lymphoma, endometrial cancer, pancreatic cancer, kidney cancer, prostate cancer, leukemia, thyroid cancer, and brain cancer.

7. The method of claim 6, wherein the composition is administered in combination with a second anti-cancer agent.

8. The method of claim 7, wherein the second anti-cancer agent is temozolamide, bevacizumab, procarbazine, lomustine, vincristine, gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vinblastine, vindesine, vinorelbine, taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, combretastatin, thalidomide, and/or lenalidomide or combinations thereof.

9. A method of imaging a tumor comprising administering a compound of claim 2 to a subject and viewing the compound by PET.

* * * * *